US006283336B1

(12) United States Patent
Dwyer et al.

(10) Patent No.: US 6,283,336 B1
(45) Date of Patent: Sep. 4, 2001

(54) ARTICLE FOR THE DELIVERY OF FOAM PRODUCTS

(75) Inventors: Jennifer Sue Dwyer, Cincinnati; James Anthony Wilson, Milford, both of OH (US); Alic Anthony Scott, Ellicott City, MD (US); Dennis Eugene Kuhlman, Middletown; Raymond Edward Bolich, Jr., Hillsboro, both of OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 09/665,833

(22) Filed: Sep. 20, 2000

Related U.S. Application Data
(60) Provisional application No. 60/154,758, filed on Sep. 20, 1999.

(51) Int. Cl.[7] .................................................. B67D 5/58
(52) U.S. Cl. ............................................................ 222/190
(58) Field of Search .................................... 222/190, 209, 222/211; 310/127

(56) References Cited

U.S. PATENT DOCUMENTS

| 3,010,613 | 11/1961 | Stossel | 222/190 |
|---|---|---|---|
| 3,134,544 | 5/1964 | Copley | 239/55 |
| 3,937,364 | 2/1976 | Wright | 222/190 |
| 4,836,422 | 6/1989 | Rosenberg | 222/190 |
| 5,064,103 | 11/1991 | Bennett | 222/190 |
| 5,071,379 | 12/1991 | Poizot | 222/464 |
| 5,672,576 | 9/1997 | Behrens et al. | 510/127 |

FOREIGN PATENT DOCUMENTS

821793 10/1959 (GB) .

Primary Examiner—Philippe Derakshani
Assistant Examiner—Thach H Bui
(74) Attorney, Agent, or Firm—Stephen T. Murphy; Jack L. Oney, Jr.

(57) ABSTRACT

The present invention relates to a low cost, article for the delivery of personal care foams comprising a package comprising a container having flexible, deformable walls, an opening portion, a first sponge having a density of from about 1.5 to about 3.0 lbs./ft$^3$; an indentation force deflection of from about 40 to about 65 lbs./50 in$^2$; and a porosity of from about 50 pores per inch to about 100 pores per inch; and a second sponge having a density of from about 1.30 to about 2.00 lbs./ft$^3$; an indentation force deflection of from about 40 to about 95 lbs./50 in$^2$; and a porosity of from about 10 pores per inch to about 50 pores per inch; and a foaming composition; wherein the ratio of the combined bulk volume of the sponges to the liquid volume of the foaming composition is from about 2:1 to about 60:1, and wherein the ratio of air volume to liquid volume is about 4:1 to about 100:1.

16 Claims, 2 Drawing Sheets

ARTICLE FOR THE DELIVERY OF FOAM PRODUCTS

This application claims the benefit of Prov. 60/154,758 filed Sep. 20, 1999.

TECHNICAL FIELD

The present invention relates to a low cost article of manufacture for the delivery of foam products, specifically personal care mousse products.

BACKGROUND OF THE INVENTION

Foaming products are well known in the art and are commercially available for a wide variety of products, such as shave cream, hair styling mousse, and body wash foam. These products are generally delivered in special packaging to create the foam. The typical example of this special packaging is pressurized packaging utilizing propellants which, when combined with the compositions, create a foam upon dispensing. Other examples of specialty packaging materials used to create foam products include air-infusing pump sprayers and bag-in-bottle technology. These aerosol and non-aerosol packages are bulky and relatively expensive to produce. It would be desirable to develop a technology which would allow the delivery of foaming personal care compositions without these special packaging devices.

U.S. Pat. No. 3,010,613, issued to Stossel on Nov. 28, 1961 discloses several devices to produce and dispense foam compositions. These devices comprise a closed deformable container with an opening portion, and a sponge element partly filling the volume of the container. These general devices cannot be generally applied to deliver a high quality foam product. Without being limited by theory, it is believed that the creation of a high quality foam is dependent on the characteristics of the foaming composition combined with specific package parameters.

In an effort to teach possible improvement options to deliver a higher quality foam, Stossel teaches several preferred package embodiments which further comprise air inlet valves, product outlet valves, multiple chambers, screens or shredded plastic. However, these additional elements increase package complexity and cost while not considering the requirements of the foaming composition.

It has been found that foam products with high quality can be delivered in a simple, low cost package by specifically combining certain foaming compositions with a package with certain critical parameters. It is the object of this invention to provide high quality personal care foams delivered from a low cost, simple package.

This and other objects and benefits of the present invention as may be set forth herein as may now or later become apparent to those skilled in the art can be provided according to the invention which is described herein.

The invention hereof can comprise, consist of, or consist essentially of the essential elements, described herein as well as any of the preferred or other optional ingredients described herein.

All percentages herein are by weight of the total composition unless otherwise indicated. All ratios are weight ratios unless otherwise indicated. Unless otherwise indicated, all percentages, ratios, and levels of ingredients referred to herein are based on the actual amount of the ingredient, and do not include solvents, fillers, or other materials with which the ingredient may be combined in commercially available products. All measurements are at 25° C. or room temperature, unless otherwise designated.

All documents referred to herein, including all patents, all patent applications, all articles, all bulletins, all pamphlets, and all technical data sheets are incorporated herein by reference in their entirety.

SUMMARY OF THE INVENTION

The present invention relates to a low cost, article for the delivery of personal care foams comprising a package comprising a container having flexible, deformable walls, an opening portion, a first sponge having a density of from about 1.5 to about 3.0 lbs./ft$^3$; an indentation force deflection of from about 40 to about 65 lbs./50 in$^2$; and a porosity of from about 50 pores per inch to about 100 pores per inch; and a second sponge having a density of from about 1.30 to about 2.00 lbs./ft$^3$; an indentation force deflection of from about 40 to about 95 lbs./50 in$^2$; and a porosity of from about 10 pores per inch to about 50 pores per inch; and a foaming composition; wherein the ratio of the combined bulk volume of the sponges to the liquid volume of the foaming composition is from about 2:1 to about 60:1, and wherein the ratio of air volume to liquid volume is about 4:1 to about 100:1. In preferred embodiments of the present invention, the foaming composition comprises an anionic surfactant; and a foam stabilizing surfactant.

DETAILED DESCRIPTION OF THE INVENTION

The article of the present invention comprises a package and a foaming composition. The compositions may be of any product desired to be in the foam form, including but not limited to hair conditioners, hair styling products, shampoos, anti-dandruff hair masks, vitamin hair masks, hair colorants, body gels, facial lotions, antibacterial lotions, shaving creams, sunscreens, fragrance masks, medication foams, bathroom cleansers, dish soaps, furniture polishes, pet groomers, laundry spot removers, carpet cleaners, shoe cleaners, and insect repellants. Preferred embodiments are personal care foams such as hair mousses or shampoos, body wash foams, handsoaps, facial cleansers, shaving creams and the like.

The term "polymeric sponge" is used herein to represent solid, polymeric foams used in the container of the present invention. The singular term "sponge" as used herein may also represent a situation where two or more pieces of the same or similar sponge material are used in the package. The term "bulk volume" of a polymeric sponge refers to the volume encompassed by the polymeric material of the sponge and the air space within the sponge. For example, the bulk volume of a rectangular solid piece of foam is simply the product of the lengths of the three sides of the solid.

The term "foam" is used herein to represent the products of the incorporation of air into a liquid foaming composition. A "high quality foam" is defined a specific foam which comprises small uniform air bubbles incorporated within the liquid composition thereby resulting in a foam which is dense, creamy and takes a relatively long time to break down.

The article of the present invention is use to produce a high quality foam product. The user of the article must prime the package by squeezing it several times before opening the package. This priming step creates the high quality, liquid foam product. The product is then dispensed through the opening portion of the container.

The essential elements, as well as a non-inclusive list of preferred and optional elements and ingredients are described below.

PACKAGE

Figure 1:
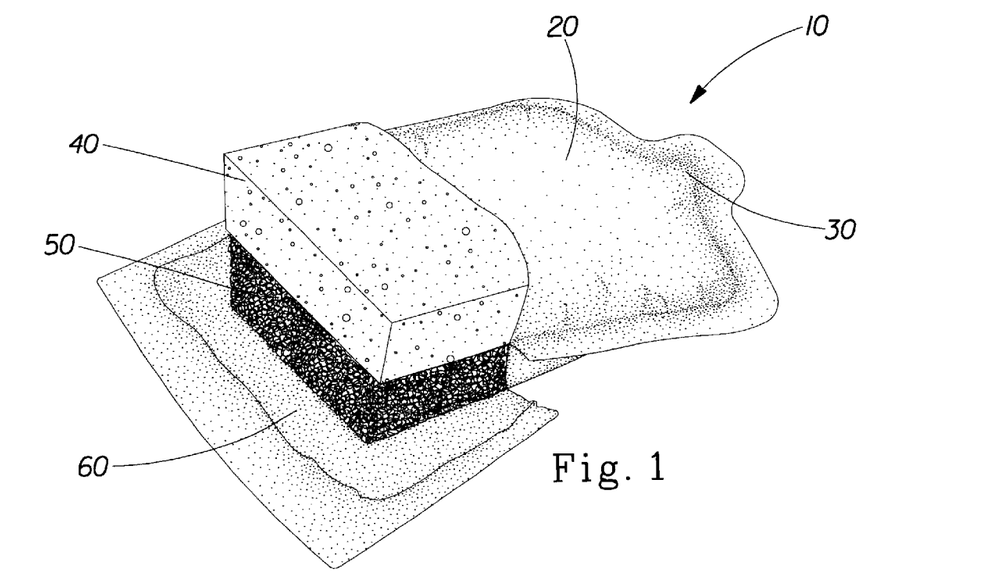
FIG. 1 is a perspective view of the package of one embodiment of the present invention, with a cut away view illustrating the first and second sponges and the foaming composition.
Figure 2:
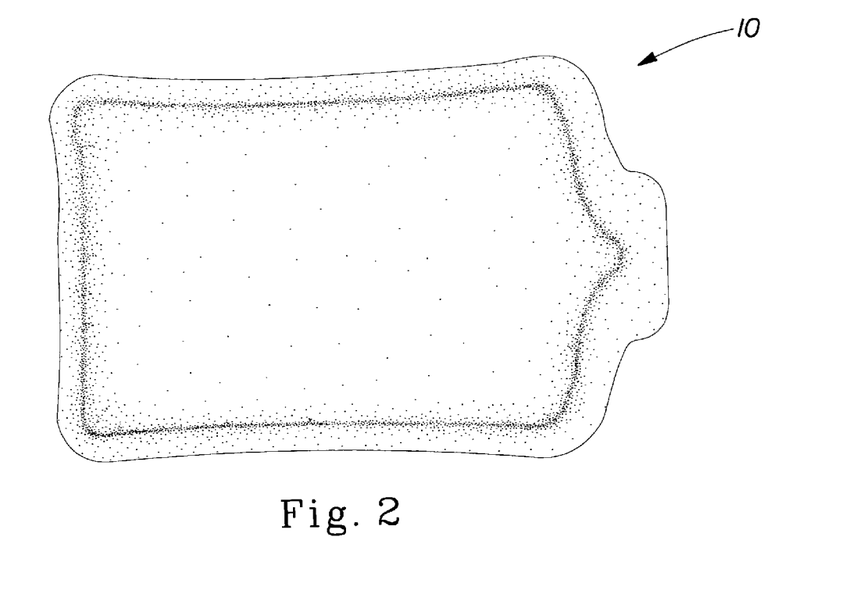
FIG. 2 is a top view of the package of one embodiment of the present invention.
Figure 3:
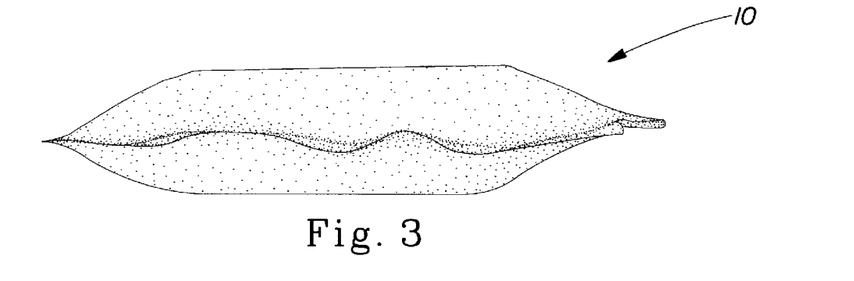
FIG. 3 is a side view of the package of one embodiment of the present invention.
Figure 4:
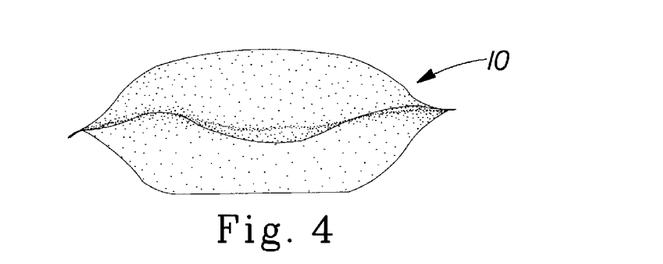
FIG. 4 is an end view of the package of one embodiment of the present invention.
Figure 5:
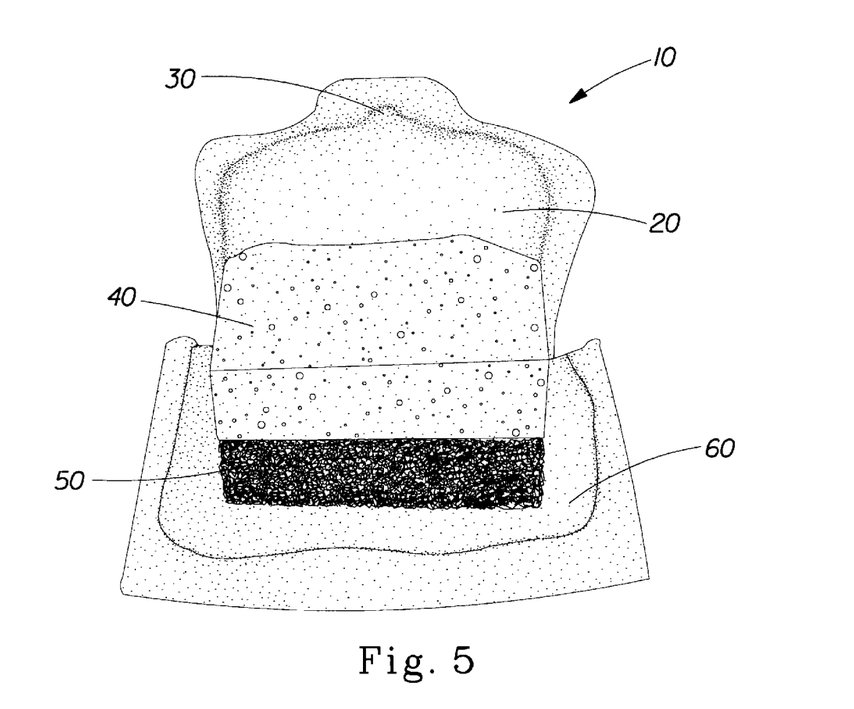
FIG. 5 is an end view of the package of one embodiment of the present invention, with a cut away view illustrating the first and second sponges and the foaming composition.

The article of the present invention comprises a package which comprises a container 10 having flexible, deformable walls 20, an opening portion 30, and a first and a second sponge 40 and 50 as depicted in FIG. 1. The package may take the form of tubes, bottles, stand-up pouches, thermoformed containers, tottles, fottles and the like.

The flexible, deformable walls 20 of the container 10 may consist of any flexible material which allows for easy deformation of the container 10 without tearing of the material. Any number of films will make a functional package in terms of generating product via priming and then dispensing. Differences in films will be barrier properties, thicknesses, and feel/texture in hands. These differences can be achieved by using single film materials or combinations of materials which are laminated together. Potentially usable films or film components include, but are not limited to, the following: nylon, polyester (PET), polypropylene (PP), polyethylene (PE), low density polyethylene (LDPE), linear low density polyethylene (LLDPE), high density polyethylene (HDPE), ethyl vinyl acetate (EVA), ethyl vinyl alcohol (EVOH), polyvinyl chloride (PVC), biaxially oriented polypropylene (BOPP), metallized oriented polypropylene (mOPP) and aluminum foil.

Different film materials allow various moisture transmission rates and oxygen barrier levels. A preferred film materials is a laminate of which the middle layer is foil. The foil layer provides virtually no moisture loss and no oxygen permeability. Thus, the foil barrier ensures package integrity over time. A large loss or gain of moisture or oxygen (air) over time may effect the internal volume ratios (i.e. sponge to liquid, etc.) which in turn may impact the foam quality of the product. Preferred laminated film materials include:

- 48 ga Polyester (PET)/Ink/9# White Coextruded Laminant/0.000285 mil Aluminum Foil/12.0 # Coextruded Laminant/Linear Low Density Polyethylene (LLDPE);
- PET 0.012 mm/Double component adhesive for dry lamination/Aluminum Foil 0.007 mm/Double component adhesive for dry lamination/LLDPE 0.050 mm.

The combination of the resilience of the polymeric sponges 40 and 50 with the resilience of the film determines the overall resilience of the total container 10. The film should be sufficiently stiff to allow for rapid resilience of the sponges 40 and 50 and for flow/mixing of air with product. Conversely, a film that completely conforms to the polyurethane foam will inhibit the flow and mixing thereby inhibiting package functionality. Depending on in-use characteristics desired i.e. slow package recovery vs. rapid package recovery, various film material/foam combinations may be optimized due to the additive nature of the resilience of these components.

The opening portion 30 of the container 10 may consist of any device or package design useful for containing the contents of the package during shipment and storage, but dispensing the foam product during use. The portion may be as simple as a section of the package which may be torn or cut away by the consumer, a resealable sealing assembly (see U.S. Pat. No. 5,938,013 issued to Palumbo et al. on Aug. 17, 1999 herein incorporated by reference), or more complex devices, such as a screw cap assembly, a flip-top assembly, a valve assembly, a push-pull assembly, a lift-off cap, a tear tape, a peel opening, or a puncture opening. The preferred opening portion 30 is a tear-away or cut-away section on the package.

The first and second sponges 40 and 50 consist of distinct polymeric sponges. Polymeric sponges according to the present invention are those which are relatively open-celled. This means the individual cells of the sponge are in complete, unobstructed communication with adjoining cells. The cells in such substantially open-celled sponge structures have intercellular openings or "windows" that are large enough to permit ready fluid transfer from one cell to the other within the sponge structure.

These substantially open-celled sponge structures will preferably have a reticulated character with the individual cells being defined by a plurality of mutually connected, three dimensionally branched webs. The strands of polymeric material making up these branched webs can be referred to as "struts." For purposes of the present invention, a sponge material is "open-celled" if at least 80% of the cells in the sponge structure that are at least 1 $\mu$m in size are in fluid communication with at least one adjacent cell.

The first and second sponge 40 and 50 may be made from any suitable resilient, compressible, porous material. Preferred sponge materials include polyurethane and cellulose, with polyurethane being most preferred.

"Sponge density" (i.e., mass of polymeric sponge material per unit volume of sponge volume in air) is specified herein on a dry basis. The density of the sponge can influence a number of performance and mechanical characteristics of the personal care foams. Any suitable gravimetric procedure that will provide a determination of mass of solid sponge or foam material per unit volume of sponge or foam structure can be used to measure the density. One procedure which can be used to determine sponge density is that described in ASTM Method No. D3574-95, Test A, which is designed primarily for the testing of urethane sponges but which can also be utilized for measuring the density of other sponges such as those of the present invention. In particular, density measurements made according to this ASTM procedure are carried out on sponge samples which have been preconditioned in a certain manner as specified in that test. Density is determined by measuring both the dry mass of a given sponge sample and its volume. Density is calculated as mass per unit volume. For purposes of this invention, density is expressed in terms of lbs./ft$^3$.

"Indentation force deflection" (IFD), as used herein, is a measure of the firmness of the polymeric sponge. IFD is measured by the "Indentation Force Deflection Test—Specified Delection", ASTM method D3574 Test B1. ASTM D3574 Test B1 describes testing for both 25% and 65% deflection. The Indentation Force Delection of the sponges of the present invention is measured only at 25% deflection. For purposes of this invention, IFD is expressed in terms of lbs./50 in$^2$. IFD and density both contribute to the total force to squeeze the article of the present invention. A sponge piece with a higher density and a lower firmness may perform relatively similarly to a foam piece with a low density and higher firmness.

"Porosity", as used herein, is a measure of the number of pores per linear inch (ppi) of the polymeric sponge. The porosity of a polymeric sponge determines the amount of fluid flow and air flow achievable through the polymeric sponge. Lower porosity indicates larger pores in the sponge and therefore more fluid flow within the sponge. Conversely, higher porosity sponges have less fluid flow within the sponge.

The first sponge 40 of the container 10 of the present invention consists of a high porosity polymeric sponge. The primary purpose of this high porosity sponge is to generate high quality foam product during the priming of the package. This foam is high quality without the need for another component, such as screens, or meshed cloths, to further modify or refine the foam product. The secondary purpose of the high porosity polymeric sponge is to serve as a reservoir for air within the package. During dispensing the high porosity sponge continues to generate high quality foam, but has limited capacity for air flow and therefore provides limited pumping action for subsequent squeezes.

The first sponge 40 therefore has a density of from about 1.5 to about 3.0 lbs./ft$^3$, preferably from about 1.75 to about 1.85 lbs./ft$^3$; an IFD of from about 40 to about 60 lbs./50 in$^2$ preferably from about 47 to about 52 lbs./50 in$^2$; and a porosity of from about 50 to about 100 ppi, preferably from about 60 to about 70 ppi. A second embodiment of the first sponge 40 preferably has a density of from about 2.6 to about 2.8 lbs./ft$^3$, and IFD of from about 40 to about 48 lbs./50 in$^2$, and a porosity of from about 75 to about 85 ppi.

The second sponge 50 of the container 10 of the present invention consists of a low porosity polymeric sponge. The primary purpose of this low porosity sponge is to serve as a reservoir for air and open area for flow of product through the package when displaced during priming. During dispensing the low porosity sponge provides most of the air flow through the package and thus drives the pumping action so the package quickly recovers between squeezes.

The second sponge 50 therefore has a density of from about 1.35 to about 2.00 lbs./ft$^3$, preferably from about 1.35 to about 1.65, and more preferably from about 1.4 to about 1.5 lbs /ft$^3$; an IFD of from about 40 to about 95 lbs./50 in$^2$, preferably from about 85 to about 95 lbs./50 in$^2$; and a porosity of from about 10 to about 50 ppi, preferably from about 10 to about 25 ppi, and more preferably from about 10 to about 20 ppi. A second embodiment of the second sponge 50 preferably has a density of from about 1.3 to about 1.65 lbs./ft$^3$, and IFD of from about 40 to about 60 lbs./50 in$^2$, and a porosity of from about 10 to about 20 ppi.

The ratio of the bulk volume of the first sponge 40 to the bulk volume of the second sponge 50 must range from about 1:2 to about 2:1, preferably from about 1:1.5 to about 1.5:1, more preferably from about 1:1.2 to about 1.2:1. The ratio of sponge bulk volumes is most preferably 1:1. Outside of this range, the core functions of each sponge (i.e. air flow, foam quality, etc.) begin to trade-off such that the end usage and functionality of the final packaged product may change.

FOAMING COMPOSITION

The article of the present invention also comprises a foaming composition 60. Preferably the foaming composition comprises an anionic surfactant and a foam stabilizing surfactant. The anionic and foam stabilizing surfactants are chosen such that they are chemically and physically compatible with the other components of the foaming composition, and do not otherwise unduly impair product aesthetics or performance. Concentrations of the two surfactants combined range from about 0% to about 50%, preferably from about 0.25% to about 20%, and more preferably from about 0.5% to about 10%, by weight of the foaming compositions.

In the present invention, a high quality foam is created by mechanical agitation which allows air to be dispersed in the liquid foaming composition. The air bubbles are separated from each other by thin liquid films. Surfactants are necessary in foam formation and stabilization because they adsorb at the interface between the air bubbles and the thin liquid film. Foams would have no stability unless there was a barrier to coalescence when two air bubbles touch. The barrier is provided by the surfactants and is due to the electrostatic repulsion and/or steric hindrance.

Foam stability is an important factor in a high quality foam. It is related to the surfactant(s) and choice of additives. It is known in the art that anionic surfactants tend to form voluminous foam. Selection of surfactants for the present invention is based upon primarily the use of anionic surfactants with other surfactants and/or electrolytes to act as foam stabilizers. Foam stabilization can be obtained either by strengthening the interfacial packing of the surfactants or by increasing the surface viscosity of the foam film so as to slow the drainage of the foam film. At the interface of the liquid film, the molecular packing and surface viscosity of the film can be increased by the addition of nonionic, cationic, amphoteric, or zwitterionic surfactants.

The addition of foam stabilizers such as nonionic, cationic, and/or amphoteric/zwitterionic surfactants to an anionic surfactant solution results in a tighter interfacial packing of the anionic surfactants by reducing charge repulsion of the head groups of the surfactants. The alkyl chain length of the foam stabilizer should be approximately the same as that of the surfactant. The addition of electrolytes and polymers of opposite charge to reduce the ionic head group electrostatic repulsion can have the same effect as adding the foam stabilizing surfactants. However, too much nonionic surfactant or electrolyte will reduce the electrical repulsion between the opposing surface films and thus reduce the foam stability. Precipitation can also result if too much oppositely charged surfactant or polymer is used as the stabilizer.

Anionic Surfactant

A wide variety of anionic surfactants are useful herein. See, e.g., U.S. Pat. No. 3,929,678, to Laughlin et al., issued Dec. 30, 1975, which is incorporated herein by reference in its entirety. Nonlimiting examples of anionic surfactants include the alkoyl isethionates, and the alkyl and alkyl ether sulfates. The alkoyl isethionates typically have the formula RCO—OCH$_2$CH$_2$SO$_3$M wherein R is alkyl or alkenyl of from about 10 to about 30 carbon atoms, and M is a water-soluble cation such as ammonium, sodium, potassium and triethanolamine. Nonlimiting examples of these isethionates include those alkoyl isethionates selected from the group consisting of ammonium cocoyl isethionate, sodium cocoyl isethionate, sodium lauroyl isethionate, sodium stearoyl isethionate, and mixtures thereof.

The alkyl and alkyl ether sulfates typically have the respective formulae ROSO$_3$M and RO(C$_2$H$_4$O)$_x$SO$_3$M, wherein R is alkyl or alkenyl of from about 10 to about 30 carbon atoms, x is from about 1 to about 10, and M is a water-soluble cation such as ammonium, sodium, potassium and triethanolamine. Examples of these materials are sodium lauryl sulfate and ammonium lauryl sulfate.

Another suitable class of anionic surfactants are the water-soluble salts of the organic, sulfuric acid reaction products of the general formula:

$R_1$—$SO_3$—M wherein $R_1$ is chosen from the group consisting of a straight or branched chain, saturated aliphatic hydrocarbon radical having from about 8 to about 24, preferably about 10 to about 16, carbon atoms; and M is a cation. Still other anionic synthetic surfactants include the class designated as succinamates, olefin sulfonates having about 12 to about 24 carbon atoms, and b-alkyloxy alkane sulfonates.

Other anionic materials useful herein are soaps (i.e. alkali metal salts, e.g., sodium or potassium salts) of fatty acids, typically having from about 8 to about 24 carbon atoms, preferably from about 10 to about 20 carbon atoms. The fatty acids used in making the soaps can be obtained from natural sources such as, for instance, plant or animal-derived glycerides (e.g., palm oil, coconut oil, soybean oil, castor oil, tallow, lard, etc.) The fatty acids can also be synthetically prepared. Soaps are described in more detail in U.S. Pat. No. 4,557,853, cited above.

Branched-chain surfactants have greater water solubility and a higher critical micelle concentration (CMC) than their linear counterparts but due to the bulkiness of the hydrophobe the intermolecular forces are weaker at the interface and the packing cannot be as tight as a linear chain surfactants. Thus, linear anionic surfactants work better for creating a more stable foam.

More preferred anionics include: alkyl and alkyl ether sulfates of structure $ROSO_3M$ and $RO(C_2H_4O)_xSO_3M$ where R is alkyl or alkenyl of from about 10 to about 18 carbon atoms, x is from about 1 to about 4 and M is a water-soluble cation most preferably $Na^+$, $K^+$, $NH_4^+$, TEA, or DEA; alkyl and alkenyl sulfonates of structure $RSO_3M$ where R is alkyl or alkenyl of from about 10 to 18 carbon atoms and other sulfonates including alkylarylsulfonates of structure $RC_6H_4SO_3M$ where R is alkyl of from about 10 to 18 carbon atoms and M is a water soluble cation most preferably $Na^+$, $K^+$, $NH_4^{+'}$, TEA, or DEA; alkyl phosphates and alkyl phosphonates of structure $ROPO_3M$ and $RPO_3M$ where R is alkyl of from about 10 to 18 carbon atoms and M is a water soluble cation most preferably $Na^+$, $K^+$, $NH_4^{+'}$, TEA, or DEA; alkyl ether phosphates of structure $RO(C_2H_4O)_xPO_3M$ where R is alkyl of from about 10 to 18 carbon atoms, x is from about 1 to about 10 and M is a water soluble cation most preferably $Na^+$, $K^+$, $NH_4^{+'}$, TEA, or DEA; alkoyl isethionates of structure $RCOOCH_2CH_2SO_3M$ where R is alkyl or alkenyl of from about 10 to 18 carbons and M is a water soluble cation most preferably $Na^+$, $K^+$, $NH_4^{+'}$, TEA, or DEA; sulfocarboxylic acid esters of structure $RO_2CCH_2SO_3M$ where R is alkyl or akenyl of from about 10 to 18 carbon atoms and M is a water soluble cation most preferably $Na^+$, $K^+$, $NH_4^{+'}$, TEA, or DEA; carboxylate soaps of fatty acid of structure RCOOM where R is alkyl or alkenyl of from about 10 to 22 carbon atoms and M is a water soluble cation most preferably $Na^+$, $K^+$, $NH_4^{+'}$, TEA, or DEA;

Even more preferred anionics include alkyl sulfates and alkyl ether sulfates of structure $ROSO_3M$ and $RO(C_2H_4O)_xSO_3M$ where R is from about 12 to 14 carbon atoms, x is from about 1 to about 4 and M is a water-soluble cation most preferably $Na^+$, $K^+$, $NH_4^+$, or TEA, including but not limited to sodium lauryl sulfate, sodium laureth(3) sulfate, ammonium lauryl sulfate, ammonium laureth(3) sulfate, potassium lauryl sulfate, potassium laureth(3) sulfate, TEA lauryl sulfate, TEA laureth(3) sulfate; alkyl and alkenyl sulfonates of structure $RSO_3M$ where R is alkyl or alkenyl of from about 12 to 16 carbon atoms and other sulfonates including alkylarylsulfonates of structure $RC_6H_4SO_3M$ where R is alkyl of from about 12 to 16 carbon atoms and M is a water soluble cation most preferably $Na^+$, $K^+$, $NH_4^{+'}$, or TEA, including but not limited to sodium C14–C16 olefin sulfonate, sodium dodecylbenzene sulfonate; alkoyl isethionates of structure $RCOOCH_2CH_2SO_3M$ where R is alkyl or alkenyl of from about 12 to 16 carbons and M is a water soluble cation most preferably $Na^+$, $K^+$, $NH_4^{+'}$, or TEA, including but not limited to sodium cocoyl isethionate; sulfocarboxylic acid esters of structure $RO_2CCH_2SO_3M$ where R is alkyl or akenyl of from about 10 to 18 carbon atoms and M is a water soluble cation most preferably $Na^+$, $K^+$, $NH_4^{+'}$, TEA, or DEA, including but not limited to sodium lauryl sulfoacetate.

Foam Stabilizing Surfactant

The foaming composition of the present invention further comprises a foam stabilizing surfactant. Nonionic, cationic, amphoteric, and zwitterionic surfactants may all be used as the foam stabilizing surfactant.

Among the nonionic surfactants that are useful herein are those that can be broadly defined as condensation products of long chain alcohols, e.g. $C_8$–$C_{30}$ alcohols, with sugar or starch polymers, i.e., glycosides. These compounds can be represented by the formula $(S)_n$—O—R wherein S is a sugar moiety such as glucose, fructose, mannose, and galactose; n is an integer of from about 1 to about 1000, and R is a $C_8$–$C_{30}$ alkyl group. Examples of long chain alcohols from which the alkyl group can be derived include decyl alcohol, cetyl alcohol, stearyl alcohol, lauryl alcohol, myristyl alcohol, oleyl alcohol, and the like. Preferred examples of these surfactants include those wherein S is a glucose moiety, R is a $C_8$–$C_{20}$ alkyl group, and n is an integer of from about 1 to about 9. Commercially available examples of these surfactants include decyl polyglucoside (available as APG 325 CS from Henkel) and lauryl polyglucoside (available as APG 600CS and 625CS from Henkel).

Other useful nonionic surfactants include the condensation products of alkylene oxides with fatty acids (i.e. alkylene oxide esters of fatty acids). When these particular nonionics are used, it is preferable to use them at low concentrations, preferably in combination with one or more of the other surfactants disclosed herein. These materials have the general formula $RCO(X)_nOH$ wherein R is a $C_8$–$C_{30}$ alkyl group, X is —$OCH_2CH_2$— or —$OCH^2CHCH_3$, and n is an integer from about 1 to about 100. Other nonionic surfactants are the condensation products of alkylene oxides with 2 moles of fatty acids (i.e. alkylene oxide diesters of fatty acids). These materials have the general formula $RCO(X)_nOOCR$ wherein R is a $C_{10}$–$C_{30}$ alkyl group, X is —$OCH_2CH_2$— (i.e. derived from ethylene glycol or oxide) or —$OCH_2CHCH_3$— (i.e. derived from propylene glycol or oxide), and n is an integer from about 1 to about 100. Other nonionic surfactants are the condensation products of alkylene oxides with fatty alcohols (i.e. alkylene oxide ethers of fatty alcohols). These materials have the general formula $R(X)nOR'$ wherein R is a $C_{10}$–$C_{30}$ alkyl group, X is —$OCH_2CH_2$— (i.e. derived from ethylene glycol or oxide) or —$OCH_2CHCH_3$— (i.e. derived from propylene glycol or oxide), and n is an integer from about 1 to about 100 and R' is H or a $C_{10}$–$C_{30}$ alkyl group. Still other nonionic surfactants are the condensation products of alkylene oxides with both fatty acids and fatty alcohols [i.e. wherein the polyalkylene oxide portion is esterified on one end with a fatty acid and etherified (i.e. connected via an ether linkage) on the other end with a fatty alcohol]. These materials have the general formula RCO(X)$_n$OR' wherein R and R' are C$_{10}$–C$_{30}$ alkyl groups, X is —OCH$_2$CH$_2$— (i.e. derived from ethylene glycol or oxide) or —OCH$_2$CHCH$_3$— (derived from propylene glycol or oxide), and n is an integer from about 1 to about 100. Nonlimiting examples of these alkylene oxide derived nonionic surfactants include ceteth-1, ceteth-2, ceteth-6, ceteth-10, ceteth-12, ceteareth-2, ceteareth-6, ceteareth-10, ceteareth-12, steareth-1, steareth-2, steareth-6, steareth-10, steareth-12, PEG-2 stearate, PEG-4 stearate, PEG-6 stearate, PEG-10 stearate, PEG-12 stearate, PEG-20 glyceryl stearate, PEG-80 glyceryl tallowate, PPG-10 glyceryl stearate, PEG-30 glyceryl cocoate, PEG-80 glyceryl cocoate, PEG-200 glyceryl tallowate, PEG-8 dilaurate, PEG-10 distearate, and mixtures thereof.

Still other useful nonionic surfactants include polyhydroxy fatty acid amide surfactants corresponding to the structural formula:

wherein: R$^1$ is H, C$_1$–C$_4$ alkyl, 2-hydroxyethyl, 2-hydroxypropyl, preferably C$_1$–C$_4$ alkyl, more preferably methyl or ethyl, most preferably methyl; R$^2$ is C$_5$–C$_{31}$ alkyl or alkenyl, preferably C$_7$–C$_{19}$ alkyl or alkenyl, more preferably C$_9$–C$_{17}$ alkyl or alkenyl, most preferably C$_{11}$–C$_{15}$ alkyl or alkenyl; and Z is a polyhydroxyhydrocarbyl moiety having a linear hydrocarbyl chain with a least 3 hydroxyls directly connected to the chain, or an alkoxylated derivative (preferably ethoxylated or propoxylated) thereof. Z preferably is a sugar moiety selected from the group consisting of glucose, fructose, maltose, lactose, galactose, mannose, xylose, and mixtures thereof. An especially preferred surfactant corresponding to the above structure is coconut alkyl N-methyl glucoside amide (i.e., wherein the R$^2$CO— moiety is derived from coconut oil fatty acids). Processes for making compositions containing polyhydroxy fatty acid amides are disclosed, for example, in G.B. Patent Specification 809,060, published Feb. 18, 1959, by Thomas Hedley & Co., Ltd.; U.S. Pat. No. 2,965,576, to E. R. Wilson, issued Dec. 20, 1960; U.S. Pat. No. 2,703,798, to A. M. Schwartz, issued Mar. 8, 1955; and U.S. Pat. No. 1,985,424, to Piggott, issued Dec. 25, 1934; which are incorporated herein by reference in their entirety.

More preferred nonionics include: alkylene oxide esters of fatty acids of structure RCO(X)$_n$OH wherein R is a C$_{10}$–C$_{30}$ alkyl group, X is —OCH$_2$CH$_2$— (ie derived from ethylene glycol or oxide) or —OCH$_2$CH$_2$CH$_2$— (ie derived from propylene glycol or oxide), and n is an integer from about 1 to 100; alkylene oxide diesters of fatty acids of structure RCO(X)$_n$OOCR; alkylene oxide ethers of fatty alcohols of structure R(X)$_n$OR' wherein R' is H or a C$_{10}$–C$_{30}$ alkyl group; condensation products of alkylene oxides with both fatty acids and fatty alcohols (i.e. wherein the polyalkylene oxide portion is esterified on one end with a fatty acid and connected via an ether linkage on the other end with a fatty alcohol of structure RCO(X)$_n$OR'; polyhydroxy fatty acid amides of structure wherein R$^1$ is H, C$_1$–C$_4$ alkyl, 2-hydroxyethyl, 2-hydroxypropyl, R$^2$ is C$_5$–C$_{31}$ alkyl or alkenyl and Z is a polyhydroxcarbyl moiety having a linear hydrocarbyl with at least 3 hydroxyls directly connected to the chain or an alkoxylated derivative thereof. Z is preferably a sugar moiety selected from the group consisting of glucose, fructose, maltose, lactose, galactose, mannose, xylose and mixtures thereof. Still other useful nonionic surfactants include alkyl or alkylene oxides of structure wherein R is a C$_{10}$–C$_{30}$ alkyl group. Still other useful nonionic surfactants include ethanolarnides of fatty acids of structure wherein R is a C$_{10}$–C$_{30}$ alkyl; diethanolamides of fatty acids of structure isopropanolamides of fatty acids of structure Most preferred nonionics include: alkyl or alkylene oxide esters of fatty acids of structure RCO(X)$_n$OH wherein R is a C$_{10}$–C$_{16}$ alkyl group, X is —OCH$_2$CH$_2$— or —OCH$_2$CH$_2$CH$_2$—, and n is an integer from about 1 to 100; alkylene oxide diesters of fatty acids of structure RCO(X)$_n$OOCR;. Nonlimiting examples of these alyklene oxide derived nonionic surfactants include laureth-4, laureth-9, undeceth-9, ceteth-1, ceteareth-2, steareth-1, steareth-2, steareth-21, PEG-2 steara PEG-6 stearate, PEG-8 dilaurate, alkyl or alkylene oxides, phosphonium oxides or sulfoxides of structure wherein R is a C$_{10}$–C$_{16}$ alkyl group such as lauramine oxide and myristamine oxide, ethanolamides of fatty acids of structure wherein R is a C$_{10}$–C$_{16}$ alkyl group such as cocamide MEA and lauramide MEA; diethanolamides of fatty acids of structure such as cocamide DEA and lauramide DEA, and mixtures thereof.

Cationic surfactants can also be utilized in the present invention. Nonlimiting examples of cationic surfactants useful herein include cationic ammonium salts such as those having the formula:

wherein $R_1$, is selected from an alkyl group having from about 12 to about 22 carbon atoms, or aromatic, aryl or alkaryl groups having from about 12 to about 22 carbon atoms; $R_2$, $R_3$, and $R_4$ are independently selected from hydrogen, an alkyl group having from about 1 to about 22 carbon atoms, or aromatic, aryl or alkaryl groups having from about 12 to about 22 carbon atoms; and X is an anion selected from chloride, bromide, iodide, acetate, phosphate, nitrate, sulfate, methyl sulfate, ethyl sulfate, tosylate, lactate, citrate, glycolate, and mixtures thereof. Additionally, the alkyl groups can also contain ether linkages, or hydroxy or amino group substituents (e.g., the alkyl groups can contain polyethylene glycol and polypropylene glycol moieties).

More preferably, $R_1$ is an alkyl group having from about 12 to about 22 carbon atoms; $R_2$ is selected from H or an alkyl group having from about 1 to about 22 carbon atoms; $R_3$ and $R_4$ are independently selected from H or an alkyl group having from about 1 to about 3 carbon atoms; and X is as described in the previous paragraph.

Most preferably, $R_1$ is an alkyl group having from about 12 to about 22 carbon atoms; $R_2$, $R_3$, and $R_4$ are selected from H or an alkyl group having from about 1 to about 3 carbon atoms; and X is as described previously.

Other ammonium quaternary and amino surfactants include those in the form of ring structures formed by covalently linking of the radicals. Examples of such cationic surfactants include imidazolines, imidazoliniums, and pyridiniums, etc., wherein said surfactant has at least one nonionic hydrophile-containing radical as set forth above. Specific examples include 2-heptadecyl-4,5-dihydro-1H-imidazol-1-ethanol, 4,5-dihydro-1-(2-hydroxyethyl)-2-isoheptadecyl-1-phenylmethylimidazolium chloride, and 1-[2-oxo-2-[[2-[(1-oxooctadecyl)oxy]ethyl]amino]ethyl] pyridinium chloride.

Alternatively, other useful cationic surfactants include amino-amides, wherein in the above structure $R_1$ is alternatively $R_5CO$—$(CH_2)_n$—, wherein $R_5$ is an alkyl group having from about 12 to about 22 carbon atoms, and n is an integer from about 2 to about 6, more preferably from about 2 to about 4, and most preferably from about 2 to about 3. Nonlimiting examples of these cationic surfactants include stearamidopropyl PG-dimonium chloride phosphate, stearamidopropyl ethyldimonium ethosulfate, stearamidopropyl dimethyl (myristyl acetate) ammonium chloride, stearamidopropyl dimethyl cetearyl ammonium tosylate, stearamidopropyl dimethyl ammonium chloride, stearamidopropyl dimethyl ammonium lactate, and mixtures thereof.

Nonlimiting examples of quaternary ammonium salt cationic surfactants include those selected from the group consisting of cetyl ammonium chloride, cetyl ammonium bromide, lauryl ammonium chloride, lauryl ammonium bromide, stearyl ammonium chloride, stearyl ammonium bromide, cetyl dimethyl ammonium chloride, cetyl dimethyl ammonium bromide, lauryl dimethyl ammonium chloride, lauryl dimethyl ammonium bromide, stearyl dimethyl ammonium chloride, stearyl dimethyl ammonium bromide, cetyl trimethyl ammonium chloride, cetyl trimethyl ammonium bromide, lauryl trimethyl ammonium chloride, lauryl trimethyl ammonium bromide, stearyl trimethyl ammonium chloride, stearyl trimethyl ammonium bromide, lauryl dimethyl ammonium chloride, stearyl dimethyl cetyl ditallow dimethyl ammonium chloride, dicetyl ammonium chloride, dicetyl ammonium bromide, dilauryl ammonium chloride, dilauryl ammonium bromide, distearyl ammonium chloride, distearyl ammonium bromide, dicetyl methyl ammonium chloride, dicetyl methyl ammonium bromide, dilauryl methyl ammonium chloride, dilauryl acetyl dimonium chloride, dilauryl methyl ammonium bromide, distearyl methyl ammonium chloride, distearyl dimethyl ammonium chloride, distearyl methyl ammonium bromide, and mixtures thereof. Additional quaternary ammonium salts include those wherein the $C_{12}$ to $C_{22}$ alkyl carbon chain is derived from a tallow fatty acid or from a coconut fatty acid. The term "tallow" refers to an alkyl group derived from tallow fatty acids (usually hydrogenated tallow fatty acids), which generally have mixtures of alkyl chains in the $C_{16}$ to $C_{18}$ range. The term "coconut" refers to an alkyl group derived from a coconut fatty acid, which generally have mixtures of alkyl chains in the $C_{12}$ to $C_{14}$ range. Examples of quaternary ammonium salts derived from these tallow and coconut sources include ditallow dimethyl ammonium chloride, ditallow dimethyl ammonium methyl sulfate, di(hydrogenated tallow) dimethyl ammonium chloride, di(hydrogenated tallow) dimethyl ammonium acetate, ditallow dipropyl ammonium phosphate, ditallow dimethyl ammonium nitrate, di(coconutalkyl)dimethyl ammonium chloride, di(coconutalkyl)dimethyl ammonium bromide, tallow ammonium chloride, coconut ammonium chloride, stearamidopropyl PG-dimonium chloride phosphate, stearamidopropyl ethyldimonium ethosulfate, stearamidopropyl dimethyl (myristyl acetate) ammonium chloride, stearamidopropyl dimethyl cetearyl ammonium tosylate, stearamidopropyl dimethyl ammonium chloride, stearamidopropyl dimethyl ammonium lactate, and mixtures thereof.

Other cationic surfactants for use in the present invention are those which are useful for providing conditioning benefits, particularly hair conditioning properties and which are quaternary ammonium or amino compounds having at least one N-radical containing one or more nonionic hydrophilic moieties selected from alkoxy, polyoxyalkylene, alkylamido, hydroxyalkyl, and alkylester moieties, and combinations thereof. The surfactant contains at least one hydrophilic moiety within 4 (inclusive), preferably within 3 (inclusive), carbon atoms of the quaternary nitrogen or cationic amino nitrogen. For purposes herein, this means that the closest non-carbon atom in the hydrophilic moiety to the cationic nitrogen must be within the stated number of carbon atoms relative to said nitrogen. Additionally, carbon atoms that are part of a hydrophilic moiety, e.g., carbon atoms in a hydrophilic polyoxyalkylene (e.g., —$CH_2$—$CH_2$—O—), that are adjacent to other hydrophilic moieties are not counted as when determining the number of hydrophilic moieties within 4, or preferably 3, carbon atoms of the cationic nitrogen. In general, the alkyl portion of any hydrophilic moiety is preferably a $C_1$–$C_3$ alkyl. Suitable hydrophile-containing radicals include, for example, ethoxy, propoxy, polyoxyethylene, polyoxypropylene, ethylamido, propylamido, hydroxymethyl, hydroxyethyl, hydroxypropyl, methylester, ethylester, propylester, or mixtures thereof, as nonionic hydrophile moieties.

Specific examples of useful quaternary ammonium salts include polyoxyethylene (2) stearyl methyl ammonium chloride, methyl bis (hydrogenated tallowamidoethyl) 2-hydroxyethyl ammonium methyl sulfate, polyoxypropylene (9) diethyl methyl ammonium chloride, tripolyoxyethylene (total PEG=10) stearyl ammonium phosphate, bis(N-hydroxyethyl-2-oleyl imidazolinium chloride) polyethylene glycol (12), and isododecylbenzyl triethanolammonium chloride.

Salts of primary, secondary and tertiary fatty amines are also useful cationic surfactant materials. The alkyl groups of such amines preferably have from about 1 to about 30 carbon atoms and must contain at least one, preferably 2 to about 10, nonionic hydrophilic moieties selected from alkoxy, polyoxyalkylene, alkylamido, hydroxyalkyl, and alkylester moieties, and mixtures thereof. Secondary and tertiary amines are preferred, tertiary amines are particularly preferred. Specific examples of suitable amines include diethyl aminoethyl polyoxyethylene (5) laurate, coco-polyglyceryl-4 hydroxypropyl dihydroxy ethylamine, and dihydroxyethyl tallowamine hydrochloride.

The cationic conditioning agents for use herein may also include a plurality of ammonium quaternary moieties or amino moieties, or a mixture thereof.

More preferred cationic foam stabilizers include: ammonium salts of structure $(R_1R_2R_3R_4N)^+X^-$ wherein $R_1$ is a $C_{12}$–$C_{22}$ alkyl group or aromatic, aryl or alkatyl group having from about 12 to 22 carbons atoms; $R_2$, $R_3$, $R_4$ are independently selected from hydrogen, a $C_1$–$C_{22}$ alkyl group, or aromatic, aryl or alkatyl group having from about 12 to 22 carbon atoms; and X is an anion selected from chloride, bromide, iodide, acetate, phosphate, nitrate, sulfate, methyl sulfate, ethyl sulfate, tosylate, lactate, glycolate, and mixtures thereof. Additionally, the alkyl groups can also contain ether linkages, or hydroxy or amino group substituents. Other useful cationics include aminoamides wherein the above structure $R_1$ is alternatively $R_5CO$—$(CH_2)_n$— wherein $R_5$ is a $C_{12}$–$C_{22}$ alkyl group and n is an integer from about 2 to about 6.

Most preferred cationic foam stabilizers include: ammonium salts of structure $(R_1R_2R_3R_4N)^+X^-$ wherein $R_1$ is a $C_{12}$–$C_{16}$ alkyl group or aromatic, aryl or alkatyl group having from about 12 to 16 carbons atoms; $R_2$, $R_3$, $R_4$ are independently selected from hydrogen, a $C_1$–$C_{16}$ alkyl group, or aromatic, aryl or alkatyl group having from about 12 to 16 carbon atoms; and X is an anion selected from chloride, bromide, iodide, acetate, phosphate, nitrate, sulfate, methyl sulfate, ethyl sulfate, tosylate, lactate, glycolate, and mixtures thereof. Additionally, the alkyl groups can also contain ether linkages, or hydroxy or amino group substituents. Other useful cationics include aminoamides wherein the above structure $R_1$ is alternatively $R_5CO$—$(CH_2)_n$— wherein $R_5$ is a $C_{12}$–$C_{16}$ alkyl group and n is an integer from about 2 to about 6. Nonlimiting examples of quaternary ammonium salt cationic surfactants include: cetyl ammonium chloride, cetyl ammonium bromide, lauryl ammonium chloride, lauryl ammonium bromide, stearyl ammonium chloride, stearyl ammonium bromide, cetyl dimethyl ammonium chloride, cetyl dimethyl ammonium bromide, lauryl dimethyl ammonium chloride, lauryl dimethyl ammonium bromide, stearyl dimethyl ammonium chloride, stearyl dimethyl ammonium bromide, cetyl trimethyl ammonium chloride, cetyl trimethyl ammonium bromide, lauryl trimethyl ammonium chloride, lauryl trimethyl ammonium bromide, stearyl trimethyl ammonium chloride, stearyl trimethyl ammonium bromide, stearyl dimethyl cetyl ammonium chloride, ditallow dimethyl ammonium chloride, dicetyl ammonium chloride, dicetyl ammonium bromide, dilauryl ammonium chloride, dilauryl ammonium bromide, distearyl ammonium chloride, distearyl ammonium bromide, dicetyl methyl ammonium chloride, dicetyl methyl ammonium bromide, dilauryl methyl ammonium chloride, dilauryl methyl ammonium bromide, distearyl methyl ammonium chloride, distearyl methyl ammonium bromide, dilauryl dimethyl ammonium chloride, distearyl dimethyl ammonium chloride, stearamidopropyl ethyl dimonium ethosulfate, stearamidopropyl dimethyl cetearyl tosylate, and mixtures thereof.

Examples of amphoteric and zwitterionic surfactants which can be used in the compositions of the present invention are those which are broadly described as derivatives of aliphatic secondary and tertiary amines in which the aliphatic radical can be straight or branched chain and wherein one of the aliphatic substituents contains from about 8 to about 22 carbon atoms (preferably $C_8$–$C_{18}$) and one contains an anionic water solubilizing group, e.g., carboxy, sulfonate, sulfate, phosphate, or phosphonate. Examples are alkyl imino acetates, and iminodialkanoates and aminoalkanoates of the formulas $RN[(CH_2)_mCO_2M]_2$ and $RNH(CH_2)_mCO_2M$ wherein m is from 1 to 4, R is a $C_8$–$C_{22}$ alkyl or alkenyl, and M is H, alkali metal, alkaline earth metal ammonium, or alkanolammonium. Also included are imidazolinium and ammonium derivatives. Specific examples of suitable amphoteric surfactants include sodium lauroamphoacetate, sodium cocoamphoacetate, sodium 3-dodecyl-aminopropionate, sodium 3-dodecylaminopropane sulfonate, N-alkyltaurines such as the one prepared by reacting dodecylamine with sodium isethionate according to the teaching of U.S. Pat. No. 2,658,072 which is incorporated herein by reference in its entirety; N-higher alkyl aspartic acids such as those produced according to the teaching of U.S. Pat. No. 2,438,091 which is incorporated herein by reference in its entirety; and the products sold under the trade name "Miranol" and described in U.S. Pat. No. 2,528,378, which is incorporated herein by reference in its entirety. Other examples of useful amphoterics include phosphates, such as coamidopropyl PG-dimonium chloride phosphate (commercially available as Monaquat PTC, from Mona Corp.).

Also useful herein as amphoteric or zwitterionic surfactants are the betaines. Examples of betaines include the higher alkyl betaines, such as coco dimethyl carboxymethyl betaine, lauryl dimethyl carboxymethyl betaine, lauryl dimethyl alphacarboxyethyl betaine, cetyl dimethyl carboxymethyl betaine, cetyl dimethyl betaine (available as Lonzaine 16SP from Lonza Corp.), lauryl bis-(2-hydroxyethyl) carboxymethyl betaine, stearyl bis-(2-hydroxypropyl) carboxymethyl betaine, oleyl dimethyl gamma-carboxypropyl betaine, lauryl bis-(2-hydroxypropyl)alpha-carboxyethyl betaine, coco dimethyl sulfopropyl betaine, stearyl dimethyl sulfopropyl betaine, lauryl dimethyl sulfoethyl betaine, lauryl bis-(2-hydroxyethyl) sulfopropyl betaine, and amidobetaines and amidosulfobetaines (wherein the $RCONH(CH_2)_3$ radical is attached to the nitrogen atom of the betaine), oleyl betaine (available as amphoteric Velvetex OLB-50 from Henkel), and cocamidopropyl betaine (available as Velvetex BK-35 and BA-35 from Henkel).

Other useful amphoteric and zwitterionic surfactants include the sultaines and hydroxysultaines such as cocamidopropyl hydroxysultaine (available as Mirataine CBS from Rhone-Poulenc), and the alkanoyl sarcosinates corresponding to the formula $RCON(CH_3)CH_2CH_2CO_2M$ wherein R is alkyl or alkenyl of about 10 to about 20 carbon atoms, and M is a water-soluble cation such as ammonium, sodium, potassium and trialkanolamine (e.g., triethanolamine).

More preferred zwitterionics surfactants in stabilizing anionic surfactants include alkylamido alkylamines of structure $RCONHCH_2CH_2NYCH_2CH_2OX$ where R is and alkyl group of about 10 to 18 carbon atoms, Y is $CH_2COOM$, $CH_2CH_2COOM$, $CH_2CHOHCH_2SO_3M$ or $CH_2CHOHCH_2OPO_3M$, X is a hydrogen or $CH_2COOM$ where M is a water soluble cation most preferably $Na^+$, $K^+$, $NH_4^{+'}$, TEA or DEA and betaines with the structure $RN^+(CH_3)_2CHCOO^-$ where R is an alkyl group from about 10 to 18 carbons or an amidopropyl alkyl group where R is from about 10 to about 18 carbons. Most preferred zwitterionic/amphoteric surfactants are disodium cocoamphodiacetate, sodium cocoamphoacetate, sodium lauroamphoacetate, cocobetaine, cocamidopropyl betaine.

Most preferred combinations of surfactants are any of the most preferred anionic surfactants at levels ranging from about 0.05% to about 25%, preferably from about 0.1% to about 10%, more preferably from about 0.25% to about 5%, most preferably from about 0.5% to about 2%, with any of the most preferred foam stabilizing surfactants at levels ranging from about 0.05% to about 30%, preferably from about 0.1% to about 15%, more preferably from about 0.25% to about 5%, most preferably from about 0.5% to about 3%. Especially preferred combinations of anionic surfactant and foam stabilizing surfactant include sodium lauryl sulfate with cocamidoproyl betaine, ammonium lauryl sulfate with cocamidopropyl betaine, TEA lauryl sulfate with cocamidopropyl betaine, potassium lauryl sulfate with cocamidopropyl betaine, sodium laureth(3) sulfate with cocamidopropyl betaine, ammonium laureth(3) sulfate with cocamidopropyl betaine, TEA laureth(3) sulfate with cocamidopropyl betaine, potassium laureth(3) sulfate with cocamidopropyl betaine, sodium lauryl sulfate with lauramide DEA, ammonium lauryl sulfate with lauramide DEA, TEA lauryl sulfate with lauramide DEA, potassium lauryl sulfate with lauramide DEA, sodium laureth(3) sulfate with lauramide DEA, ammonium laureth(3) sulfate with lauramide DEA, TEA laureth(3) sulfate with lauramide DEA, and potassium laureth(3) sulfate with lauramide DEA. Even more especially preferred is the combination of sodium lauryl sulfate with cocamidopropyl betaine.

OPTIONAL PERSONAL CARE AGENT

The foaming composition of the article of the present invention may further comprise from about 0.1% to about 50%, preferably from about 0.5% to about 25%, more preferably from about 1% to about 15% of a personal care agent. Selection of the specific agent is dependent on the type of personal care composition desired.

Hair Styling or Hair Shine Agents

The personal care agent of the foaming compositions of the present invention may comprise any polymer soluble or colloidally dispersible in water. If an optional cosolvent, such as ethanol, is present, the polymer should be soluble or dispersible in the combined solvent system. Solubility or dispersibility is determined at ambient conditions. Suitable types of polymers include anionic, nonionic, amphoteric, and cationic. Mixtures of polymers may also be used. With certain of the polymers it may be necessary to neutralize some acidic groups to promote solubility/dispersibility.

Suitable cationic polymers include Polyquatemium-4 (Celquat H-100; L200—supplier National Starch); Polyquaternium-10 (Celquat SC-240C; SC-230 M—supplier National Starch); (UCARE polymer series—JR-125, JR-400, LR-400, LR-30M, LK, supplier Amerchol); Polyquaternium-11 (Gafquat 734; 755N—supplier ISP); Polyquaternium-16 (Luviquat FC 370; FC550; FC905; HM-552 supplier by BASF); PVP/Dimethylaminoethylmethacrylate (Copolymer 845; 937; 958—ISP supplier); Vinyl Caprolactam/PVP/Dimethylaminoethyl Methacrylate copolymer (Gaffix VC-713; H2OLD EP-1—supplier ISP); Chitosan (Kytamer L; Kytamer PC—supplier Amerchol); Polyquaternium-7 (Merquat 550—supplier Calgon); Polyquaternium-18 (Mirapol AZ-1 supplied by Rhone-Poulenc); Polyquaternium-24 (Quatrisoft Polymer LM-200—supplier Amerchol); Polyquaternium-28 (Gafquat HS-100—supplier ISP); Polyquaternium-46 (Luviquat Hold—supplier BASF); and Chitosan Glycolate (Hydagen CMF; CMFP—supplier Henkel); Hydroxyethyl Cetyldimonium Phosphate (Luviquat Mono CP—supplier BASF); and Guar Hydroxylpropyl Trimonium Chloride (Jaguar C series-13S, -14S, -17, 162,-2000, Hi-CARE 1000—supplier Rhone-Poulenc).

Suitable amphoteric polymers include Octylacrylmide/Acrylates/Butylaminoethyl Methacrylate Copolymer (Amphomer 28-4910, Amphomer LV-71 28-4971, Lovocryl-47 28-4947—National Starch supplier), and Methacryloyl ethyl betaine/methacrylates copolymer (Diaformer series supplier Mitsubishi).

Polymers which are partially zwitterionic are also useful. They possess a positive charge over a broad range of pH but contain acidic groups which are only negatively charged at basic pH. The polymer is positively charged at lower pH and neutral (have both negative and positive charge) at higher pHs. The zwitterionic polymer may be selected from cellulose derivatives, wheat derivatives and chitin derivatives such as are known in the art. Nonlimiting examples of zwitterionic polymers useful herein include Polyquaternium-47 (Merquat 2001—supplier Calgon (a zwitterionic copolymer of acrylic acid, methacryl amido propyl trimethyl ammonium chloride, and methyl acrylate)); Carboxyl Butyl Chitosan (Chitolam NB/101—marketed by Pilot Chemical Company, developed by Lamberti); and Dicarboxyethyl Chitosan (N-[(3'-hydroxy-2',3'-dicarboxy) ethyl]-beta-D-(1,4)-glucosamine) (available from Amerchol as, e.g., CHITOLAM NB/101).

Useful nonionic polymers include PVP or Polyvinylpyrrolidone (PVP K-15, K-30, K-60, K-90, K-120—supplier ISP) (Luviskol K series 12, 17, 30, 60, 80, & 90—supplier BASF); PVP/VA (PVP/VA series S-630; 735, 635, 535, 335, 235—supplier ISP )(Luviskol VA); PVP/DMAPA acrylates copolymer (Styleze CC-10—supplier ISP); PVP/VA/Vinyl Propionate copolymer (Luviskol VAP 343 E, VAP 343 I, VAP 343 PM—supplier BASF); Hydroxylethyl Cellulose (Cellosize HEC—supplier Amerchol); and Hydroxylpropyl Guar Gum (Jaguar HP series-8, -60, -105, -120—supplier Rhône-Poulenc).

Anionic polymers suitable for use herein include VA/Crotonates/Vinyl Neodecanonate Copolymer (Resyn 28-2930—National Starch supplier); Butyl Ester of PVM/MA (Gantrez A-425; ES-425; ES-435—supplier ISP); Ethyl Ester of PVM/MA (Gantrez ES-225; SP-215—supplier ISP); Acrylates/acrylamide copolymer (Luvimer 100P; Lumiver Low VOC, supplier BASF); Methacrylate Copolymer (Balance 0/55-National Starch supplier); Vinyl Acetate/Crotonic Acid copolymer (Luviset CA 66—supplier BASF); Isopropyl Ester of PVM/MA Copolymer (Gantrez ES-335—supplier ISP); Acrylates Copolymer; Methacrylates/acrylates copolymer/amine salt (Diahold polymers— supplier Mitsubishi); 2-Butenedioic Acid (Z)-, Monoethyl Ester, Polymer with Methoxyethene (Omnirez 2000); VA/Butyl maleate/Isobornyl Acrylate (Advantage Plus terpolymer—supplier ISP); Acrylates Copolymer (Amerhold DR-25—supplier Amerchol); Acrylates/Hydroxyesteracrylates Copolymer (Acudyne 255 supplier Rohm & Haas); vinyl Acetate/Crotonic Acid/Vinyl Propionate copolymer (Luviset CAP—supplier BASF); PVP/Acrylates copolymer (Luviflex VBM 35—supplier BASF); Diglycol/CHDM/Isophthalates/SIP Copolymer (Eastman AQ 48, AQ 55—supplier Eastman Chemicals); Acrylates/Octacrylamide Copolymer (Versatyl-42 or Amphomer HC-National Starch supplier); TBA/AA copolymer (75/25—Mitsubishi Chemical Corp.); Acrylates Copolymer (Aculyn 33—supplier Rohm & Haas); Acrylates/Steareth-20 Methacrylate Copolymer (Aculyn 22—supplier Rohm & Haas); and Carbomer (supplier B. F. Goodrich).

Hair styling polymer(s) concentrations may range from about 0.1% to about 30%, preferably from about 0.3% to about 25%, more preferably from about 0.5% to about 20%, by weight of the composition. These styling polymers provide the foaming composition of the present invention with hair styling performance by providing polymeric deposits on the hair after application. The polymer deposited on the hair has adhesive and cohesive strength and delivers styling primarily by forming welds between hair fibers upon drying, as is understood by those skilled in the art.

Many such polymers are known in the art, including water-insoluble organic polymers and water-insoluble silicone-grafted polymers, all of which are suitable for use in the foaming composition herein, provided that they also have the requisite features or characteristics described hereinafter. Such polymers can be made by conventional or otherwise known polymerization techniques well known in the art, an example of which includes free radical polymerization.

Examples of suitable organic and silicone grafted polymers for use in the foaming composition of the present invention are described in greater detail hereinafter.

I. Organic Styling Polymer

The hair styling polymers suitable for use in the foaming composition of the present invention include organic hair styling polymers well known in the art. The organic styling polymers may be homopolymers, copolymers, terpolymers or other higher polymers, but must comprise one or more polymerizable hydrophobic monomers to thus render the resulting styling polymer hydrophobic and water-insoluble as defined herein. The styling polymers may therefore further comprise other water soluble, hydrophillic monomers provided that the resulting styling polymers have the requisite hydrophobicity and water insolubility.

The organic styling polymers preferably have a weight average molecular weight of at least about 20,000, preferably greater than about 25,000, more preferably greater than about 30,000, most preferably greater than about 35,000. There is no upper limit for molecular weight except that which limits applicability of the invention for practical reasons, such as processing, aesthetic characteristics, formulateability, etc. In general, the weight average molecular weight will be less than about 10,000,000, more generally less than about 5,000,000, and typically less than about 2,000,000. Preferably, the weight average molecular weight will be between about 20,000 and about 2,000,000, more preferably between about 30,000 and about 1,000,000, and most preferably between about 40,000 and about 500,000.

Examples of other suitable styling polymers are described in U.S. Pat. No. 5,120,531, to Wells et al., issued Jun. 9, 1992; U.S. Pat. No. 5,120,532, to Wells et al., issued Jun. 9, 1992; U.S. Pat. No. 5,104,642, to Wells et al., issued Apr. 14, 1992; U.S. Pat. No. 4,272,511, to Papantoniou et al., issued Jun. 9, 1981; U.S. Pat. No. 5,672,576, to Behrens et al., issued Sep. 30, 1997; and U.S. Pat. No. 4,196,190, to Gehman et al., issued Apr. 1, 1980, which descriptions are incorporated herein by reference.

II. Silicone-grafted Styling Polymer

Other suitable styling polymers for use in the foaming composition of the present invention are silicone-grafted hair styling resins. These polymers may be used alone or in combination with the organic styling polymers described hereinbefore. Many such polymers suitable for use in the foaming composition herein are known in the art. These polymers are characterized by polysiloxane moieties covalently bonded to and pendant from a polymeric carbon-based backbone.

The backbone of the silicone-grafted polymer is preferably a carbon chain derived from polymerization of ethylenically unsaturated monomers, but can also be cellulosic chains or other carbohydrate-derived polymeric chains to which polysiloxane moieties are pendant. The backbone can also include ether groups, ester groups, amide groups, urethane groups and the like. The polysiloxane moieties can be substituted on the polymer or can be made by copolymerization of polysiloxane-containing polymerizable monomers (e.g. ethylenically unsaturated monomers, ethers, and/or epoxides) with non-polysiloxane-containing polymerizable monomers.

The silicone-grafted styling polymers for use in the foaming composition comprise "silicone-containing" (or "polysiloxane-containing") monomers, which form the silicone macromer pendant from the backbone, and non-silicone-containing monomers, which form the organic backbone of the polymer.

Preferred silicone-grafted polymers comprise an organic backbone, preferably a carbon backbone derived from ethylenically unsaturated monomers, such as a vinyl polymeric backbone, and a polysiloxane macromer (especially preferred are polydialkylsiloxane, most preferably polydimethylsiloxane) grafted to the backbone. The polysiloxane macromer should have a weight average molecular weight of at least about 500, preferably from about 1,000 to about 100,000, more preferably from about 2,000 to about 50,000, most preferably about 5,000 to about 20,000. Organic backbones contemplated include those that are derived from polymerizable, ethylenically unsaturated monomers, including vinyl monomers, and other condensation monomers (e.g., those that polymerize to form polyamides and polyesters), ring-opening monomers (e.g., ethyl oxazoline and caprolactone), etc. Also contemplated are backbones based on cellulosic chains, ether-containing backbones, etc.

Preferred silicone grafted polymers for use in the foaming composition comprise monomer units derived from: at least one free radically polymerizable ethylenically unsaturated monomer or monomers and at least one free radically polymerizable polysiloxane-containing ethylenically unsaturated monomer or monomers.

The silicone grafted polymers suitable for use in the foaming composition generally comprise from about 1% to about 50%, by weight, of polysiloxane-containing monomer units and from about 50% to about 99% by weight, of non-polysiloxane-containing monomers. The non-polysiloxane-containing monomer units can be derived from the hydrophilic and/or hydrophobic monomer units described hereinbefore.

The styling polymer for use in the foaming composition can therefore comprise combinations of the hydrophobic and/or polysiloxane-containing monomer units described herein, with or without hydrophilic comonomers as described herein, provided that the resulting styling polymer has the requisite characteristics as described herein.

Suitable polymerizable polysiloxane-containing monomers include, but are not limited to, those monomers that conform to the formula:

wherein X is an ethylenically unsaturated group copolymerizable with the hydrophobic monomers described herein, such as a vinyl group; Y is a divalent linking group; R is a hydrogen, hydroxyl, lower alkyl (e.g. $C_1$–$C_4$), aryl, alkaryl, alkoxy, or alkylamino; Z is a monovalent siloxane polymeric moiety having a number average molecular weight of at least about 500, which is essentially unreactive under copolymerization conditions, and is pendant from the vinyl polymeric backbone described above; n is 0 or 1; and m is an integer from 1 to 3. These polymerizable polysiloxane-containing monomers have a weight average molecular weight as described above.

A preferred polysiloxane-containing monomer conforms to the formula:

wherein m is 1, 2 or 3 (preferably m=1); p is 0 or 1; q is an integer from 2 to 6; $R^1$ is hydrogen, hydroxyl, lower alkyl, alkoxy, alkylamino, aryl, or alkaryl (preferably $R^1$ is alkyl); X conforms to the formula wherein $R^2$ is hydrogen or —COOH (preferably $R^2$ is hydrogen); $R^3$ is hydrogen, methyl or —CH2COOH (preferably $R^3$ is methyl); Z conforms to the formula:

wherein $R^4$, $R^5$, and $R^6$ independently are lower alkyl, alkoxy, alkylamino, aryl, arylalkyl, hydrogen or hydroxyl (preferably $R^4$, $R^5$, and $R^6$ are alkyls); and r is an integer of about 5 or higher, preferably about 10 to about 1500 (most preferably r is from about 100 to about 250). Most preferably, $R^4$, $R^5$, and $R^6$ are methyl, p=0, and q=3.

Another preferred polysiloxane monomer conforms to either of the following formulas wherein: s is an integer from 0 to about 6, preferably 0, 1, or 2, more preferably 0 or 1; m is an integer from 1 to 3, preferably 1; $R^2$ is C1–C10 alkyl or $C_7$–$C_{10}$ alkylaryl, preferably $C_1$–$C_6$ alky $C_7$–$C_{10}$ alkylaryl, more preferably $C_1$–$C_2$ alkyl; n is an integer from 0 to 4, preferably 0 or 1, more preferably 0.

The silicone grafted styling polymers suitable for use in the foaming composition preferably comprise from about 50% to about 99%, more preferably from about 60% to about 98%, most preferably from about 75% to about 95%, by weight of the polymer, of non-silicone macromer-containing monomer units, e.g. the total hydrophobic and hydrophilic monomer units described herein, and from about 1% to about 50%, preferably from about 2% to about 40%, more preferably from about 5% to about 25%, of silicone macromer-containing monomer units, e.g. the polysiloxane-containing monomer units described herein. The level of hydrophilic monomer units can be from about 0% to about 70%, preferably from about 0% to about 50%, more preferably from about 0% to about 30%, most preferably from about 0% to about 15%; the level of hydrophobic monomer units, can be from 30% to about 99%, preferably from about 50% to about 98%, more preferably from about 70% to about 95%, most preferably from about 85% to about 95%.

Examples of some suitable silicone grafted polymers for use in the foaming composition herein are listed below. Each listed polymer is followed by its monomer composition as weight part of monomer used in the synthesis:

(i) t-butylacrylatye/t-butyl-methacrylate/2-ethylhexyl-methacrylate/PDMS macromer-20,000 molecular weight macromer 31/27/32/10

(ii) t-butylmethacrylate/2-ethylhexyl-methacrylate/PDMS macromer-15,000 molecular weight macromer 75/10/15

(iii) t-butylmethacrylate/2-ethylhexyl-acrylate/PDMS macromer-10,000 molecular weight macromer 65/15/20

(iv) t-butylacrylate/2-ethylhexyl-acrylate/PDMS macromer-14,000 molecular weight macromer 77/11/12

(v) t-butylacrylate/2-ethylhexyl-methacrylate/PDMS macromer-13,000 molecular weight macromer 81/9110

Examples of other suitable silicone grafted polymers for use in the foaming composition of the present invention are described in EPO Application 90307528.1, published as EPO Application 0 408 311 A2 on Jan. 11, 1991, Hayama, et al.; U.S. Pat. No. 5,061,481, issued Oct. 29, 1991, Suzuki et al.; U.S. Pat. No. 5,106,609, Bolich et al., issued Apr. 21, 1992; U.S. Pat. No. 5,100,658, Bolich et al., issued Mar. 31, 1992; U.S. Pat. No. 5,100,657, Ansher-Jackson, et al., issued Mar. 31, 1992; U.S. Pat. No. 5,104,646, Bolich et al., issued Apr. 14, 1992; U.S. Ser. No. 07/758,319, Bolich et al, filed Aug. 27, 1991, U.S. Ser. No. 07/758,320, Torgerson et al., filed Aug. 27, 1991, which descriptions are incorporated herein by reference.

The polyol copolymers comprise a liquid or semisolid hair styling agent suitable for being left on dry hair as a liquid or semisolid after the composition has been applied and allowed to dry on the hair. These hair styling agents provide for a fluid film to be left on the hair which can be characterized as a reformable weld that provides dry hair restyling performance without the need to reapply the compositions or add additional styling aids on the hair.

The concentration of the polyol copolymer may vary with each selected hair styling formulation, but such concentrations will generally range from about 3% to about 50%, more preferably from about 5% to about 25%, even more preferably from about 7% to about 15%, by weight of the composition.

Suitable styling agents for use in the foaming compositions of the present invention include any known or otherwise effective hair styling agents, other than polyalkylene glyceryl ethers, that are liquids or semisolids under ambient conditions and that can remain a liquid or semisolid after the composition has been applied and allowed to dry on dry hair. It has been found that certain liquid or semisolid styling agents, particularly low molecular weight polyalkylene glycols, can leave a fluid film on the hair that allows the hair fibers to be separated by forces such as wind, and then re-adhere using styling techniques such as combing, brushing, or running your fingers through the hair. This separation/readherence property provided by the styling agents defined herein results in improved dry hair restyling performance for several days without leaving the hair feeling unduly sticky or stiff, and without having to reapply the compositions described herein and/or add any other additional styling aids on the hair.

Nonlimiting examples of styling agents suitable for use in the foamong compositions of the present invention include water-soluble materials such as polyalkylene glycols, polyethylene/polypropylene glycol copolymers, polyethylene/polypropylene diol copolymers, polyglycerins, and mixtures thereof, and/or their derivatives, and/or mixtures thereof, including the water-soluble polyalkylene glyceryl ethers which are also liquids or semisolids under ambient conditions. In this context, the term "water-soluble" refers to those styling materials that have a solubility in water at 25° C. of greater than 0.6%, preferably greater than 1.0%, more preferably greater than about 1.5% by weight.

Preferred styling agents suitable for use herein include those water-soluble polyalkylene glycols which conform to the formula:

wherein R is selected from the group consisting of H, methyl, and mixtures thereof. When R is H, these materials are polymers of ethylene oxide, which are also known as polyethylene oxides, polyoxyethylenes, and polyethylene glycols. When R is methyl, these materials are polymers of propylene oxide, which are also known as polypropylene oxides, polyoxypropylenes, and polypropylene glycols. When R is methyl, it is also understood that various positional isomers of the resulting polymers can exist.

In the above structure, n has an average value of from 4 to about 35, preferably from about 5 to about 35, more preferably from about 5 to about 30, and even more preferably from about 5 to about 20.

Specific examples of preferred polyalkylene glycol polymers include polyethylene/polypropylene glycol copolymers (e.g., methoxy, ethoxy, propoxy, butoxy, and pentoxy, polyethylene/polypropylene glycols), triglycerin, hexaglycerin, PPG4, PPG-6, PEG-5, PEG-6, PEG-8, PEG-12, PEG-14, PEG-18, PEG-20, PEG-32, and mixtures thereof. Most preferred are those polyalkylene glycols which have a number average molecular weight of from about 190 to about 1500, preferably from about 300 to about 1200, more preferably from about 400 to about 1000; and from about 5 to about 35, preferably from about 5 to about 30, more preferably from about 5 to about 20, repeating alkylene oxide radicals wherein each of the repeating alkylene oxide radicals has from 2 to 6 carbon atoms. Specific examples of the most preferred polyalkylene glycols include, but are not limited to, PPG4 wherein R equals methyl and n has an average value of about 4; PEG-8 wherein R equals H and n has an average value of about 8 (PEG-8 is also known as Carbowax 400, which is available from Union Carbide); PEG-12 wherein R equals H and n has an average value of about 12 (PEG-12 is also known as Carbowax 600, which is available from Union Carbide); and PEG-20 wherein R equals H and n has an average value of about 20 (PEG-20 is also known as Carbowax 900, which is available from Union Carbide).

The personal care agent of the foaming composition of the present invention may comprise from about 0.1% to about 30%, preferably from about 4% to about 25%, more preferably from about 5% to about 20%, and most preferably from about 7% to about 15% of a hair shine enhancer. The hair shine enhancer may be a 1, 2 $C_5$–$C_8$-alkane diol, a $C_2$–$C_{10}$-alkyl glyceryl ether, polyol copolymes, or a mixture thereof.

The 1,2 $C_5$–C8-alkane diols are compounds of the formula:

where $R^1$ is an propyl, butyl, pentyl, or hexyl group. $R^1$ may be straight chain or branched groups, preferably straight chain. The preferred alkane diols are 1,2 n-pentane diol, 1,2 n-hexane diol, 1,2 n-heptane diol, or mixtures thereof. Most preferred is 1,2 n-hexane diol, where $R^1$ is n-butyl.

The $C_2$–$C_{10}$-alkyl glyceryl ethers are compounds of the formula:

where $R^2$ is an ethyl, propyl, butyl, pentyl, hexyl, heptyl, octyl, nonyl, or decyl group. $R^2$ may be straight chain or branched groups, preferably straight chain. The preferred glyceryl ethers are n-propyl-, n-butyl-, n-pentyl-, n-hexyl glycerol ethers and mixtures thereof. Most preferred is n-hexyl glyceryl ether.

Emollients and Skin Conditioning Agents

A wide variety of lipid type materials and mixtures of materials are suitable for use as the personal care agent of the foaming composition of the present invention. Preferably, the lipophilic skin conditioning agent is selected from the group consisting of hydrocarbon oils and waxes, silicones, fatty acid derivatives, cholesterol, cholesterol derivatives, di- and tri-glycerides, vegetable oils, vegetable oil derivatives, liquid nondigestible oils such as those described in U.S. Pat. No. 3,600,186 to Mattson; Issued Aug. 17, 1971 and U.S. Pat. Nos. 4,005,195 and 4,005,196 to Jandacek et al; both issued Jan. 25, 1977, all of which are herein incorporated by reference, or blends of liquid digestible or nondigestible oils with solid polyol polyesters such as those described in U.S. Pat. No. 4,797,300 to Jandacek; issued Jan. 10, 1989; U.S Pat. Nos. 5,306,514, 5,306,516 and 5,306,515 to Letton; all issued Apr. 26, 1994, all of which are herein incorporated by reference, and acetoglyceride esters, alkyl esters, alkenyl esters, lanolin and its derivatives, milk tri-glycerides, wax esters, beeswax derivatives, sterols, phospholipids and mixtures thereof.

Hydrocarbon oils and waxes may be used as the personal care agent. Some examples are petrolatum, mineral oil micro-crystalline waxes, polyalkenes (e.g. hydrogenated and nonhydrogenated polybutene and polydecene), paraffins, cerasin, ozokerite, polyethylene and perhydrosqualene. Blends of petrolatum and hydrogenated and nonhydrogenated high molecular weight polybutenes wherein the ratio of petrolatum to polybutene ranges from about 90:10 to about 40:60 are also suitable for use as the lipid skin moisturizing agent in the compositions herein.

Silicone Oils may also be used in the personal care agent. Some examples are dimethicone copolyol, dimethylpolysiloxane, diethylpolysiloxane, high molecular weight dimethicone, mixed $C_1$–$C_{30}$ alkyl polysiloxane, phenyl dimethicone, dimethiconol, and mixtures thereof. More preferred are non-volatile silicones selected from dimethicone, dimethiconol, mixed $C_1$–$C_{30}$ alkyl polysiloxane, and mixtures thereof. Nonlimiting examples of silicones useful herein are described in U.S. Pat. No. 5,011,681, to Ciotti et al., issued Apr. 30, 1991, which is incorporated by reference.

Alkyl and alkenyl esters may also be used as the personal care agent. Some examples are methyl, isopropyl and butyl esters of fatty acids; hexyl laurate, isohexyl laurate, isohexyl palmitate, decyl oleate, isodecyl oleate, hexadecyl stearate, diisopropyl adipate, diisobutly adipate, diisohexyl adipate, dihexadecy adipate, diisopropyl sebacte, lauryl lactate, myristyl lactate, cetyl lactate, oleyl myristate, oleyl stearate, and oleyl oleate.

Fatty acids, fatty alchohols and fatty alcohol ethers may also be used as the personal care agent. Some examples are lauric, myristic, palmitic, stearic, isostearic, hydroxystearic, oleic, linoleic, ricinoleic, arachidic, behenic, erucic and lanolin acids; lauryl myristyl, cetyl, hexadecyl, stearyl, isostearyl, hydroxystearyl, oleyl, ricinoleyl, behenyl, erucyl, 2-octyl dodecanol and lanolin alcohols; and ethoxylated lauryl, cetyl, stearyl, isostearyl, oleyl, lanolin alcohols and propoxylated lauryl, cetyl, stearyl, isostearyl, oleyl, lanolin alcohols.

Lanolin and its derivatives may also be used as the personal care agent. Some examples are: lanolin, lanolin oil, lanolin wax, isoproply lanolate, ethoxylated lanolin, ethoxylated lanolin alcohols, propoxylated lanolin alcohols, ethoxylated hydrogenated lanolin, and ethoxylated sorbitol lanolin.

Polyols and Polyether derivatives may also be use as the personal care agent. Some examples include: propylene glycol, dipropylene glycol, polypropylene glycol 2000, 4000, polyoxyethlene polyoxypropylene glycols, polyoxypropylene polyoxyethylene glycols, glycerol, ethoxylated glycerol, propoxylated glycerol, sorbitol, ethoxylated sorbitol, hydroxypropyl sorbitol, polyethylene glycol 200–6000, methoxy polyethylen glycols 350, 550, 750, 2000, 5000, polyethylene oxide homopolymers (mol wt 100000–5000000), polyalkylene glycols and derivatives, hexylene glycol, 1,3-butylene glycol, 1,2,6-hexantetriol, ethohexadiol (2-ethyl-1,3-hexanediol), and C15–C18 vicinal glycol Polyol esters may also be used as the personal care agent. Some examples include ethylene glycol mono- and di-fatty acid esters, diethylene glycol mono- and di-fatty acid esters, polyethylene glycol (200–6000) mono- and di-fatty acid esters, propylene glycol mono-and di-fatty acid esters, polypropylene glycol 2000 monooleate, polypropylene glycol 2000 monostearate, ethoxlyated propylene glycol monostearate, glyceryl mono- and di-fatty acid esters, polyglycerol poly-fatty acid esters, ethoxylated glyceryl monostearate, 1,3-butylene glycol monostearate, 1,3-butylene glycol distearate, polyoxyethylene polyol fatty acid ester, sorbitan fatty acid esters, and polyoxyethylene sorbitan fatty acid esters.

Other examples of skin conditioning personal care agents include di- and tri-glycerides such as castor oil, soy bean oil, soybean oils, safflower oil, cotton seed oil, corn oil, walnut oil, eanut oil, olive oil, cod liver oil, almond oil, avocado oil, palm oil and sesame oil, vegetable oils and vegetable oil derivatives; coconut oil and derivatized coconut oil, cottonseed oil and derivatized cottonseed oil, jojoba oil, cocoa butter, acetoglyceride esters, lanolin and its derivatives, and the like.

Antimicrobial Agents

The personal care agent may consist of an antimicrobial agent from about 0.1% to 30% more preferred from about 0.25% to 25% and most preferred 0.5% to 10%. Many different types of antimicrobial agents may be used among them include: phenols and cresols such as 2,4-dichloro-symmetaxylenol, parachlorometaxylenol, parachlorometacresol and other chloroxylenols and chlorocresols; bisphenols such as hexachlorophene (2,2'-methylene-bis-(3,4,6-trichlorphenol)), dichlorophene (2,2'-methylene-bis-(4-chlorphenol)), bithionol (2,2'-thiobis-(4,6-dichlorophenol)), triclosan (2,4,4'-trichloro-2"-hydoxydiphenylether)); and fentichlor ((Bis-($^2$-hyroxy-5-chlorophenyl) sulfide); salicylanilides such as 4',5-dibromsalicylanilide, 3',4',5-trichlorosalicylanilide, 3,4',5-tribromosalicylanilide, and 3,5,dibromo-3'-trifluoromethylsalicylanilide; carbanilides such as trichlorocarbanilde (3,4,4' trichlorocarbanilide) and 3-trifluoromethyl-4-4'-dichlorocarbanilide; quaternary ammonium compounds such as alkyl-dimethyl benzyl ammonium chloride, alkyl-trimethyl ammonium chloride, alkyl trimethyl ammonium bromide, cetyl-trimethyl ammonium bromide, B-phenoxyethyl-dimethyl-dodecyl ammonium bromide, p-tert-octylphenoxyethoxyethyl-dimethylbenzyl ammonium chloride, tetradecyl-pyridinium bromide, cetyl pyridinium bromide, cetyl pyridinium chloride, di-(n-octyl)-dimethyl ammonium bromide, alkyl-isoquinolinium bromide, 1-(3-chloroallyl)-3-5-7-triaza-1-azoniaadamantane chloride, and chlorhexidine (1,6,di(N-p-chlorophenylguanidino)hexane). Other antimicrobial agents include 2-bromo-2-nitropropan-1,3-diol, imidazonidyl urea, ethanol, and isopropyl alchol.

UV Absorbers/Sunscreen Agents

UV absorbers and sunscreen agents may be used as the personal care agent in the foaming compostion. Some examples include: p-aminobenzoic acid and its derivatives (ethyl, isobutyl, glycerly esters), p-dimethylaminobenzoic acid and its derivitatives (ethyl, isobutyl, glyceryl esters), o-aminobenzoates and its derivatives (methyl, menthyl, phenyl, benzyl, phenylethyl, linaly, terpenyl, and cyclohexenyl esters), salicylates (amyl, phenyl, benzyl, menthyl, glyceryl, and dipropylene-glycol esters), cinnamic acid derivatives (menthyl and benzyl esters; alphphenyl cinnamonitrile; butly cinnamoyl pyruvate, 2-ethylhexyl p-methoxycinnamate, iso-amyl p-methoxycinnamate), dihydroxycinnamic acid derivatives (umbelliferone, methylumbelliferone, methylaceto-umbelliferone), trihydroxycinnamic acid derivatives (esculetin, methylesculetin, daphnetin), hydrocarbons (diphenylbutadiene, stilbene), dibenzalacetone, benzalacetophenone, naphthosulphonates (sodium salts of 2-naphthol-3,6-disulphonic acid and of 2-naphthol-6,8-disulphonic acid), organic benzophenone derivatives (2,4-dihydroxybenzophenone, 2,2',4,4'-tetrahydroxybenzophenone, 2-hydroxy-4-methoxybenzophenone, 2-hydroxy-4-methoxybenzophenone-5-sulfonic acid, 2,2'-dihydroxy-4,4'-dimethoxybenzophenone, 2,2'-dihydroxy-4-methoxybenzophenone, disodium 2,2'-dihydroxy-4,4'-dimethoxy-5,5'-disulfobenzophenone), zinc oxide, titainium dioxide Hair Color Agents Hair coloring dyes may be used as the personal care agent in the foaming composition. Some examples include: nitrophenylenediamines compounds such as nitro-p-phenylene diamine, 4-amino-3-nitro-N-methylaniline, 4-amino-3-nitro-N-(2-hydroxyethyl)aniline, 4-(2-hydroxyethyl)amino-3-nitro-aniline, 4-(2-hydroxyethyl)amino-3-nitro-N-(2-hydroxyethyl)aniline, 4-(2-hydroxyethyl)amino-3-nitro-N, N-[bis-(2-hydroxyethyl)]aniline, 4-methylamino-3-nitro-N, N-[bis-(2-hydroxyethyl)]aniline, 4-methylamino-3-nitro-N-methyl-N-(2-hydroxyethyl)aniline, 4-nitro-o-phenylene diamine, 2-amino-4-nitro-N-(2-hydroxyethyl)aniline, 2-(2-hydroxyethyl)amnino-4-nitro-N-(2-hydroxyethyl)-aniline, 2-amino-4-nitro-N-[tris-(hydroxymethyl)]nmethyl aniline, 4-nitro-m-phenylene diamine; nitroaminophenol compounds such as 2-amino-4-nitro-phenol, 2-amino-4,6-dinitro-phenol, 2-amino-5-nitro-phenol, 2-(2-hydroxyethyl) amino-5-nitro-phenol methyl ether, 2-(2-hydroxyethyl) amino-5-nitro-phenol-2-hydroxyethyl ether, 4-amino-2-nitro-phenol, 4-methylamino-2-nitro-phenol, 4-methylamino-2,6-dinitrophenol, 4-amino-3-nitro-phenol, 4-(2-hydroxyethyl)amino-3-nitro-phenol, 4-(2-hydroxyethyl)amino-3-nitro-phenol methyl ether, 4-amino-3-nitro-phenol-2-hydroxyethyl ether; aminoanthraquinones such as 1-amino-4-methylamino anthraquinone, 1,4-diamino-5-nitro anthraquinone, 1,4,5,8-tetra amino anthraquinone, 1-methylamino-4-(2-hydroxyethyl)amino anthraquinone, 1-hydroxy-2,4-diamino anthraquinone.

Insect Repellents:

Insect repellents may be used as the personal care agent in the foaming composition. Some examples include: dimethyl carbate, ethylhexanediol, dimethyl phthalate, 2-ethyl-1,3-hexanediol, bisbutylene tetrahydrofurfural, and N,N-diethyl-m-toluamide.

Other Optional Ingredients

The foaming composition may also comprise of other nonessential, optional components suitable for rendering such compositions more acceptable for the application. Such conventional optional ingredients are well known to those skilled in the art e.g. preservatives such as benzyl alcohol, phenoxyethanol, methyl paraben, propyl paraben, DMDM hydantoin, imidazolidinyl urea; thickeners and viscosity modifiers such as diethanolamide of a long chain fatty acid, fatty alcohold (i.e. cetearyl alcohol), sodium chloride, sodium sulfate, ethyl alcohol; hydroxyethyl cellulose, Carbomer, pH adjusting agents such as citric acid, sodium citrate dihydrate, succinic acid, sodium hydroxide, triethanolamine; coloring agents such as any of the FD&C or D&C dyes; hair oxidizing (bleaching) agents such as hydrogen peroxide, perborate salts and persulfate salts; hair reducing agents such as the thioglycolates; perfume oils; and chelating agents such as disodium EDTA.

Ratio of Bulk Volume of Sponge to Volume of Foaming Composition

The ratio of the combined bulk volume of the first and second sponges 40 and 50 to the volume of liquid foaming composition preferably ranges from about 12:1 to about 30:1, preferably from about 14:1 to about 25:1, more preferably from about 16:1 to about 19:1.

Ratio of Air Volume of Liquid Volume within the Article

The ratio of the volume of air within the package and to the liquid volume of the foaming composition preferably ranges from about 4:1 to about 100:1, preferably from about 10:1 to about 80:1, more preferably from about 15:1 to about 60:1, and most preferably from about 25:1 to about 40:1.

METHODS OF MANUFACTURE AND USE OF THE PERSONAL CARE FOAM ARTICLES

Foaming Compositions

EXAMPLE 1

Hair Styling Mousse Composition

| Ingredient | Weight Percent |
| --- | --- |
| Water-USP Purified | q.s. |
| PEG-12 | 15.00 |
| Sodium Lauryl Sulfate (29% active) | 2.21 |
| Cocamidopropyl Betaine (30% active) | 2.87 |
| DMDM Hydantoin (55% active) | 0.37 |

-continued

| Ingredient | Weight Percent |
| --- | --- |
| Methylparaben | 0.20 |
| Fragrance | 0.15 |
| Disodium EDTA | 0.12 |
| Propylparaben | 0.10 |
| Hydroxyethyl Cellulose | 0.10 |
| Sodium Citrate, Dihydrate | 0.09 |
| Citric Acid, Powder | 0.05 |

The composition of Example 1 is made by adding water and heating to approximately 155° F. With agitation, add the methyl paraben, propyl paraben, disodium EDTA and hydroxyethyl cellulose, each time waiting for the indredients to dissolve/melt prior to adding the next ingredient. After hydroxyethyl cellulose is dissolved shut off heat and continue mixing. With agitation add citric acid, sodium citrate, sodium lauryl sulfate, cocamidopropyl betaine, PEG-12, DMDM Hydantoin, and perfume, each time waiting for the ingredients to dissolve/melt prior to adding the next. Stir for approximately 15 minutes to ensure uniformity.

EXAMPLE 2

Hair Styling Mousse Composition

| Ingredient | Weight Percent |
| --- | --- |
| Water-USP Purified | q.s. |
| PEG-8 | 15.00 |
| Dilauryl acetyl dimonium chloride | 5.00 |
| Phenoxyethanol | 0.60 |
| Benzyl Alcohol | 0.50 |
| Sodium Cocoyl Isethionate | 0.25 |
| Fragrance | 0.15 |
| Disodium EDTA | 0.12 |

The composition of Example 2 is made by adding water and heating to approximately 80° F. With agitation, add the following ingredients in order each time waiting for any solids to dissolve/melt prior to adding the next ingredient: sodium cocoyl isethionate, PEG-8, Dilauryl acetyl dimonium chloride, disodium EDTA, phenoxyethanol, benzyl alcohol, and perfume. Stir for approximately 15 minutes to ensure uniformity.

EXAMPLE 3

Hair Styling Mousse Composition

| Ingredient | Weight Percent |
| --- | --- |
| Water-USP Purified | q.s. |
| PVP/VA (50%) | 6.00 |
| Glycerine | 6.00 |
| Sodium Lauryl Sulfate (29% active) | 1.72 |
| Propylene Glycol | 1.00 |
| Polyquaterium 22 | 2.00 |
| Phenoxyethanol | 0.30 |
| Benzyl Alcohol | 0.50 |
| Polyquaternium 4 | 0.50 |
| Disodium EDTA | 0.12 |
| Fragrance | 0.10 |

The composition of Example 3 is made by adding water and heating to approximately 130° F. With agitation, add the following ingredients in order each time waiting for any solids to dissolve/melt prior to adding the next ingredient: PVP/VA, Polyquaterniium 4, sodium lauryl sulfate, glycerine, propylene glycol, Polyquaternium 22, disodium EDTA, phenoxyethanol, benzyl alcohol, and perfume. Stir for approximately 15 minutes to ensure uniformity.

EXAMPLE 4

Antibaterial Hand Sanitizing Foam

| Water-USP Purified | q.s. |
|---|---|
| Triclosan | 0.30 |
| Glycerine | 10.00 |
| Sodium Lauryl Sulfate (29% active) | 3.45 |
| Cocamidopropyl Betaine (30% active) | 4.47 |
| DMDM Hydantoin (55% active) | 0.37 |
| Methylparaben | 0.20 |
| Fragrance | 0.15 |
| Disodium EDTA | 0.12 |
| Propylparaben | 0.10 |
| Hydroxyethyl Cellulose | 0.10 |

The composition of Example 4 is made by adding water and heating to approximately 155° F. With agitation, add the methyl paraben, propyl paraben, disodium EDTA and hydroxyethyl cellulose, each time waiting for the indredients to dissolve/melt prior to adding the next ingredient. After hydroxyethyl cellulose is dissolved shut off heat and continue mixing. With agitation add sodium lauryl sulfate, cocamidopropyl betaine. Premix glycerine and triclosan in a separate container and add to main mix with agitation. Continue agitation and add DMDM Hydantoin and perfume. Stir for approximately 15 minutes to ensure uniformity.

EXAMPLE 5

Insect Repelling Skin Conditioning Foam

| Water-USP Purified | q.s. |
|---|---|
| 2-ethyl-1,3-hexanediol | 5.50 |
| Glycerine | 10.00 |
| Sodium Lauryl Sulfate (29% active) | 3.45 |
| Cocamidopropyl Betaine (30% active) | 4.47 |
| DMDM Hydantoin (55% active) | 0.37 |
| Methylparaben | 0.20 |
| Fragrance | 0.15 |
| Disodium EDTA | 0.12 |
| Propylparaben | 0.10 |
| Hydroxyethyl Cellulose | 0.10 |

The composition of Example 5 is made by adding water and heating to approximately 155° F. With agitation, add the methyl paraben, propyl paraben, disodium EDTA and hydroxyethyl cellulose, each time waiting for the indredients to dissolve/melt prior to adding the next ingredient. After hydroxyethyl cellulose is dissolved shut off heat and continue mixing. With agitation add sodium lauryl sulfate, cocamidopropyl betaine. Premix glycerine and 2-ethyl-1,3-hexanediol in a separate container and add to main mix with agitation. Continue agitation and add DMDM Hydantoin and perfume. Stir for approximately 15 minutes to ensure uniformity.

EXAMPLE 6

Acne Medication Foam Composition

| Water-USP Purified | q.s. |
|---|---|
| Salicylic Acid | 2.00 |
| Glycerine | 5.00 |
| Sodium Lauryl Sulfate (29% active) | 3.45 |
| Cocamidopropyl Betaine (30% active) | 4.47 |
| DMDM Hydantoin (55% active) | 0.37 |
| Methylparaben | 0.20 |
| Fragrance | 0.15 |
| Disodium EDTA | 0.12 |
| Propylparaben | 0.10 |
| Hydroxyethyl Cellulose | 0.10 |

The composition of Example 6 is made by adding water and heating to approximately 155° F. With agitation, add the methyl paraben, propyl paraben, disodium EDTA and hydroxyethyl cellulose, each time waiting for the indredients to dissolve/melt prior to adding the next ingredient. After hydroxyethyl cellulose is dissolved shut off heat and continue mixing. With agitation add salicylic acid, sodium lauryl sulfate, cocamidopropyl betaine, DMDM Hydantoin, and perfume, each time waiting for the ingredients to dissolve/melt prior to adding the next. Stir for approximately 15 minutes to ensure uniformity.

EXAMPLE 7

Shaving Foam Composition

| Water-USP Purified | q.s. |
|---|---|
| Stearic Acid | 7.00 |
| Triethanolamine | 3.50 |
| Sodium Lauryl Sulfate | 2.00 |
| Cocamidopropyl Betaine (30% active) | 2.60 |
| Fragrance | 0.25 |
| Dimethicone Copolyol | 1.00 |
| Disodium EDTA | 0.12 |
| Propylparaben | 0.10 |

Packages

EXAMPLE 8

Reticulated, polyurethane sponge having a density of 1.80 lbs./ft$^3$, an IFD of 50 lbs./50 in$^2$, and a porosity of 65 is cut into a rectangular solid having a length of 3 inches, a width of 2 inches, and a thickness of 0.625 inches. Reticulated, polyurethane sponge having a density of 1.45 lbs./ft$^3$, an IFD of 90 lbs./50 in$^2$, and a porosity of 15 is cut into a second rectangular solid having a length of 3 inches, a width of 3 inches, and a thickness of 0.75 inches. 48 ga PET/Ink/9# White Coextruded Laminant/0.000285 Aluminum Foil/12.0# Coextruded Laminant/LLDPE film is cut into two five-sided pieces, each piece having two parallel sides being 4.5 inches long, with those sides connected by a third side 3.5 inches long at one end and two equal fourth and fifth sides 1.825 inches long, creating a point at the other end. (FIG. 1) The two pieces of sponge are placed between the two pieces of film and the edges of the film is heat sealed along the two 4.5 inch and two 1.825 inch sides, leaving the 3.5 inch side open. 10 cm$^3$ of any of the foaming compositions from Examples 1–7 is added to the package. Finally the 3.5 inch side is sealed, enclosing the sponges and composition.

The article is used by manually squeezing the package for 10 to 20 seconds, cutting or tearing away the end of the point of the package and again squeezing the package to deliver the foam product.

EXAMPLE 9

Reticulated, polyurethane sponge having a density of 2.70 lbs./ft$^3$, an IFD of 45 lbs./50 in$^2$, and a porosity of 80 is cut into a rectangular solid having a length of 3 inches, a width of 3 inches, and a thickness of 0.75 inches. Reticulated, polyurethane sponge having a density of 1.45 lbs./ft$^3$, an IFD of 50 lbs./50 in$^2$, and a porosity of 15 is cut into a second rectangular solid having a length of 3 inches, a width of 3 inches, and a thickness of 0.75 inches. 48 ga PET/Ink/9# White Coextruded Laminant/0.000285 Aluminum Foil/12.0# Coextruded Laminant/LLDPE film is cut into two five-sided pieces, each piece having two parallel sides being 4.5 inches long, with those sides connected by a third side 3.5 inches long at one end and two equal fourth and fifth sides 1.825 inches long, creating a point at the other end. (FIG. 1) The two pieces of sponge are placed between the two pieces of film and the edges of the film is heat sealed along the two 4.5 inch and two 1.825 inch sides, leaving the 3.5 inch side open. 10 cm$^3$ of any of the foaming compositions from Examples 1–7 is added to the package. Finally the 3.5 inch side is sealed, enclosing the sponges and composition.

The article is used by manually squeezing the package for 10 to 20 seconds, cutting or tearing away the end of the point of the package and again squeezing the package to deliver the foam product.

EXAMPLE 10

Reticulated, cellulose sponge having a density of 1.80 lbs./ft$^3$, an IFD of 50 lbs./50 in$^2$, and a porosity of 65 is cut into a rectangular solid having a length of 3 inches, a width of 3 inches, and a thickness of 0.75 inches. Reticulated, polyurethane sponge having a density of 1.45 lbs./ft$^3$, an IFD of 90 lbs./50 in$^2$, and a porosity of 15 is cut into a second rectangular solid having a length of 3 inches, a width of 3 inches, and a thickness of 0.75 inches. 48 ga PET/Ink/9# White Coextruded Laminant/0.000285 Aluminum Foil/12.0# Coextruded Laminant/LLDPE film is cut into two five-sided pieces, each piece having two parallel sides being 4.5 inches long, with those sides connected by a third side 3.5 inches long at one end and two equal fourth and fifth sides 1.825 inches long, creating a point at the other end. (FIG. 1) The two pieces of sponge are placed between the two pieces of film and the edges of the film is heat sealed along the two 4.5 inch and two 1.825 inch sides, leaving the 3.5 inch side open. 10 cm$^3$ of any of the foaming compositions from Examples 1–7 is added to the package. Finally the 3.5 inch side is sealed, enclosing the sponges and composition.

The article is used by manually squeezing the package for 10 to 20 seconds, cutting or tearing away the end of the point of the package and again squeezing the package to deliver the foam product.

EXAMPLE 11

Reticulated, polyurethane sponge having a density of 1.80 lbs./ft$^3$, an IFD of 50 lbs./50 in$^2$, and a porosity of 65 is cut into a rectangular solid having a length of 3 inches, a width of 3 inches, and a thickness of 0.75 inches. Reticulated, polyurethane sponge having a density of 1.45 lbs./ft$^3$, an IFD of 90 lbs./50 in$^2$, and a porosity of 15 is cut into a second rectangular solid having a length of 3 inches, a width of 3 inches, and a thickness of 0.75 inches. PET 0.012 mm/Double component adhesive for dry lamination/Aluminum Foil 0.007 mm/Double component adhesive for dry lamination/LLDPE 0.050 mm film is cut into two five-sided pieces, each piece having two parallel sides being 4.5 inches long, with those sides connected by a third side 3.5 inches long at one end and two equal fourth and fifth sides 1.825 inches long, creating a point at the other end. (FIG. 1) The two pieces of sponge are placed between the two pieces of film and the edges of the film is heat sealed along the two 4.5 inch and two 1.825 inch sides, leaving the 3.5 inch side open. 10 cm$^3$ of any of the foaming compositions from Examples 1–7 is added to the package. Finally the 3.5 inch side is sealed, enclosing the sponges and composition.

The article is used by manually squeezing the package for 10 to 20 seconds, cutting or tearing away the end of the point of the package and again squeezing the package to deliver the foam product.

What is claimed is:

1. An article for the delivery of foam products comprising:
   a. a package comprising:
      i. flexible, deformable walls;
      ii. an opening portion;
      iii. a first sponge having a porosity of from about 50 pores per inch to about 100 pores per inch; and
      iv. a second sponge having a porosity of from about 10 pores per inch to about 50 pores per inch; and
   b. a foaming composition;
   wherein the ratio of the combined bulk volume of the sponges to the liquid volume of the foaming composition is from about 12:1 to about 30:1;
   wherein the walls of the package are sealed such that the first and second sponges and the foaming composition are fully contained within the walls and such that the opening portion, when utilized, provides a pathway to deliver the foaming composition from the package.

2. An article according to claim 1 wherein the ratio of air volume to liquid volume ranges from about 4:1 to about 100:1.

3. An article according to claim 1 wherein the foaming composition comprises an anionic surfactant and a foam stabilizing surfactant.

4. An article according to claim 1 wherein the first sponge further has a density of from about 1.5 to about 3.0 lbs./ft$^3$ and an indentation force deflection of from about 40 to about 52 lbs./50 in$^2$, and the second sponge further has a density of from about 1.35 to about 1.65 lbs./ft$^3$ and an indentation force deflection of from about 40 to about 95 lbs./50 in$^2$.

5. An article according to claim 4 wherein the walls of the container is selected from the group consisting of 48 ga PET/Ink/9# White Coextruded Laminant/0.000285 mil Aluminum Foil/12.0# Coextruded Laminant/LLDPE film, and PET 0.012 mm/Double component adhesive for dry lamination/Aluminum Foil 0.007 mm/Double component adhesive for dry lamination/LLDPE 0.050 mm film.

6. An article according to claim 4 wherein the first sponge has a density of from about 1.75 to about 1.85 lbs./ft$^3$, an indentation force deflection of from about 47 to about 52 lbs./50 in$^2$, and a porosity of from about 60 pores per inch to about 70 pores per inch; and the second sponge has a density of from about 1.4 to about 1.5 lbs./ft$^3$, an indentation force deflection of from about 85 to about 95 lbs./50 in$^2$, and a porosity of from about 10 pores per inch to about 20 pores per inch.

7. An article according to claim 4 wherein the first sponge has a density of from about 2.6 to about 2.8 lbs./ft$^3$, an indentation force deflection of from about 40 to about 48 lbs./50 in$^2$, and a porosity of from about 75 pores per inch to about 85 pores per inch; and the second sponge has a density of from about 1.3 to about 1.65 lbs./ft$^3$, an indentation force deflection of from about 40 to about 60 lbs./50 in$^2$, and a porosity of from about 10 pores per inch to about 20 pores per inch.

8. An article according to claim 1 wherein the opening portion is selected from the group consisting of a screw cap assembly, a flip-top assembly, a valve assembly, a push-pull assembly, a lift-off cap, a tear-away section or a cut-away section.

9. An article according to claim 8 wherein the opening portion is selected from the group consisting of a tear-away section or a cut-away section.

10. An article according to claim 6 wherein the anionic surfactant is selected from the group consisting of sodium lauryl sulfate, sodium laureth(3) sulfate, ammonium lauryl sulfate, ammonium laureth(3) sulfate, potassium lauryl sulfate, potassium laureth(3) sulfate, TEA lauryl sulfate, TEA laureth(3) sulfate, sodium C14–C16 olefin sulfonate, sodium dodecylbenzene sulfonate, sodium cocoyl isethionate, sodium lauryl sulfoacetate, and mixtures thereof.

11. An article according to claim 10 wherein the foam stabilizing surfactant is selected from the group consisting of ceteth-1, ceteth-2, ceteth-6, ceteth-10, ceteth-12, ceteareth-2, ceteareth-6, ceteareth-10, ceteareth-12, steareth-1, steareth-2, steareth-6, steareth-10, steareth-12, PEG-2 stearate, PEG-4 stearate, PEG-6 stearate, PEG-10 stearate, PEG-12 stearate, PEG-20 glyceryl stearate, PEG-80 glyceryl tallowate, PPG-10 glyceryl stearate, PEG-30 glyceryl cocoate, PEG-80 glyceryl cocoate, PEG-200 glyceryl tallowate, laureth-4, laureth-9, undeceth-9, ceteth-1, ceteareth-2, steareth-1, steareth-2, steareth-21, PEG-2 stearate, PEG-6 stearate, PEG-8 dilaurate PEG-8 dilaurate, PEG-10 distearate, lauramine oxide, myristamine oxide, cocamide MEA and lauramide MEA, cocamide DEA, lauramide DEA sodium cocoyl isethionate disodium cocoamphodiacetate, sodium cocoamphoacetate, sodium lauroamphoacetate, cocobetaine, cocamidopropyl betaine, cetyl ammonium chloride, cetyl ammonium bromide, lauryl ammonium chloride, lauryl ammonium bromide, stearyl ammonium chloride, stearyl ammonium bromide, cetyl dimethyl ammonium chloride, cetyl dimethyl ammonium bromide, lauryl dimethyl ammonium chloride, lauryl dimethyl ammonium bromide, stearyl dimethyl ammonium chloride, stearyl dimethyl ammonium bromide, cetyl trimethyl ammonium chloride, cetyl trimethyl ammonium bromide, lauryl trimethyl ammonium chloride, lauryl trimethyl ammonium bromide, stearyl trimethyl ammonium chloride, stearyl trimethyl ammonium bromide, stearyl dimethyl cetyl ammonium chloride, ditallow dimethyl ammonium chloride, dicetyl ammonium chloride, dicetyl ammonium bromide, dilauryl ammonium chloride, dilauryl ammonium bromide, distearyl ammonium chloride, distearyl ammonium bromide, dicetyl methyl ammonium chloride, dicetyl methyl ammonium bromide, dilauryl methyl ammonium chloride, dilauryl methyl ammonium bromide, distearyl methyl ammonium chloride, distearyl methyl ammonium bromide, dilauryl dimethyl ammonium chloride, distearyl dimethyl ammonium chloride, stearamidopropyl ethyl dimonium ethosulfate, stearamidopropyl dimethyl cetearyl tosylate, and mixtures thereof.

12. A article according to claim 7 wherein the foaming surfactant is selected from the group consisting of sodium lauryl sulfate, sodium laureth(3) sulfate, ammonium lauryl sulfate, ammonium laureth(3) sulfate, TEA lauryl sulfate, TEA laureth(3) sulfate, potassium lauryl sulfate, potassium laureth(3) sulfate, and mixtures thereof; and the foam stabilizing surfactant is selected from the group consisting of cocamidopropyl betaine, lauramide DEA, and mixtures thereof.

13. An article according to claim 3 wherein the foaming composition further comprises a personal care agent.

14. An article according to claim 13 wherein the personal care agent is selected from the group consisting of hair styling agents, hair shine agents, emollients, skin conditioning agents, antimicrobial agents, UV absorbers, sunscreen agents, hair color agents, insect repellants, and mixtures thereof.

15. A low cost, article for the delivery of foam products comprising:
   a. a package comprising:
      i. a container having flexible, deformable walls selected from the group consisting of 48 ga PET/Ink/9# White Coextruded Laminant/0.000285 Aluminum Foil/12.0# Coextruded Laminant/LLDPE film and PET 0.012 mm/Double component adhesive for dry lamination/Aluminum Foil 0.007 mm/Double component adhesive for dry lamination/LLDPE 0.050 mm film;
      ii. an opening portion selected from the group consisting of a tear-away section or a cut-away section;
      iii. a first sponge having a density of from about 1.5 to about 3.0 lbs./ft$^3$; an indentation force deflection of from about 40 to about 52 lbs./50 in$^2$; and a porosity of from about 60 pores per inch to about 100 pores per inch; and
      iv. a second sponge having a density of from about 1.35 to about 1.65 lbs./ft$^3$; an indentation force deflection of from about 40 to about 95 lbs./50 in$^2$; and a porosity of from about 10 pores per inch to about 25 pores per inch; and
   b. a foaming composition comprising:
      i. an anionic surfactant selected from the group consisting of sodium lauryl sulfate, sodium laureth(3) sulfate, ammonium lauryl sulfate, ammonium laureth(3) sulfate, TEA lauryl sulfate, TEA laureth(3) sulfate, potassium lauryl sulfate, potassium laureth (3) sulfate, and mixtures thereof; and
      ii. a foam stabilizing surfactant selected from the group consisting of cocamidopropyl betaine, lauramide DEA, and mixtures thereof; wherein the ratio of the combined bulk volume of the sponges to the liquid volume of the foaming composition is from about 12:1 to about 30:1; wherein the walls of the package are sealed such that the first and second sponges and the foaming composition are fully contained within the walls and such that the opening portion, when utilized, provides a pathway to deliver the foaming composition from the package.

16. An Article according to claim 15 wherein the foaming compositions comprises from about 0.05% to about 25% sodium lauryl sulfate and from about 0.05% to about 30% cocamidopropyl betaine.

* * * * *